(12) United States Patent
Brown

(10) Patent No.: US 8,078,257 B2
(45) Date of Patent: Dec. 13, 2011

(54) COMPLEX AMPLITUDE MODULATION IN BLOOD FLOW AND PERFUSION MEASUREMENT FOR MEASURING A DISTRIBUTION OF TRANSIT TIMES ON A VOXEL BY VOXEL BASIS

(75) Inventor: Truman R. Brown, Cornwall-on-Hudson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 896 days.

(21) Appl. No.: 11/684,338

(22) Filed: Mar. 9, 2007

(65) Prior Publication Data

US 2007/0282193 A1     Dec. 6, 2007

Related U.S. Application Data

(60) Provisional application No. 60/781,501, filed on Mar. 9, 2006.

(51) Int. Cl.
*A61B 5/05* (2006.01)
(52) U.S. Cl. ........ 600/419; 600/407; 600/410; 324/306; 324/307; 324/309
(58) Field of Classification Search .................. 600/407, 600/410, 419; 324/306, 307, 309, 318, 322
See application file for complete search history.

(56) References Cited

U.S. PATENT DOCUMENTS

| | | | |
|---|---|---|---|
| 3,786,341 A * | 1/1974 | Anderson et al. | 324/311 |
| 5,865,746 A * | 2/1999 | Murugesan et al. | 600/410 |
| 6,549,007 B1 | 4/2003 | Hills et al. | |
| 2004/0133927 A1 | 7/2004 | Sternberg et al. | |

OTHER PUBLICATIONS

Calamante, F. et al., Measuring Cerebral Blood Flow Using Magnetic Resonance Imaging Techniques, Journal of Cerebral Blood Flow and Metablolism, (1999) 19, 701-735.*
Barbier, E. et al., Methodology of Brain Perfusion Imaging, Journal of Magnetic Resonance Imaging, (2001) 13, 496-520.*
Petersen, E. et al., Model-Free Arterial Spin Labeling Quantification Approach for Perfusion MRI, Magnetic Resonance in Medicine, (2006) 55, 219-232.*
Golay, X. et al., Perfusion Imaging Using Arterial Spin Labeling, Topics in Magnetic Resonace Imaging, (2004) 15, 10-27.*
Barbier, E. et al., Perfusion Analysis Using Dynamic Arterial Spin Labeling (DASL), Magnetic Resonance in Medicine 41:299-308 (1999).*
Barbier, E. et al., Methodology of Brain Perfusion Imaging, Journal of Magnetic Resonance Imaging 13; 496-520 (2001).*

(Continued)

*Primary Examiner* — Brian Casler
*Assistant Examiner* — Rajeev Siripurapu
(74) *Attorney, Agent, or Firm* — Baker Botts LLP

(57) ABSTRACT

Systems and methods for blood flow and perfusion measurement using complex amplitude modulation of MRI pulses are presented. In exemplary embodiments of the disclosed subject matter, inflowing arterial spins can be modulated using a complex modulation function having certain mathematical properties in the frequency domain, such as, for example, a pseudo-random sequence. In exemplary embodiments of the disclosed subject matter the mathematical properties of such complex modulation functions can be used to measure individual transit times by deconvolving them from a series of acquired images. In exemplary embodiments of the disclosed subject matter images can be acquired at the same rapid rate as arterial modulation, and transit time distribution in the imaged tissue can be determined as part of a single integrated acquisition.

27 Claims, 11 Drawing Sheets

Schematic of an exemplary PRAM scheme. The first row represents the PRS, the second the desired magnetization, the third and fourth the time step and image acquisitions, and the bottom row indicates when the 180° pulses must be applied to achieve the desired magnetization.

OTHER PUBLICATIONS

Ogawa, S., Lee, T. M., Kay, A R. & Tank, D. W. Brain magnetic resonance imaging with contrast dependent on blood oxygenation. Proc Natl Acad Sci U S A 87, 9868-72 (1990).

Kety, S. S. & Schmidt, C. F. The determination of cerebral blood flow in man by use of nitrous oxide in low concentrations. Am J Physiol. 143, 53-66 (1945).

Ito, H., Kanno, I. & Fukuda, H. Human cerebral circulation: positron emission tomography studies. Ann Nucl Med 19, 65-74 (2005).

Williams, D. S., Detre, J. A. Leigh, J. S. & Koretsky, A. P. Magnetic resonance imaging of perfusion using spin inversion of arterial water. Proc Natl Acad Sci U S A 89, 212-6 (1992).

Kwong, K. K., Wanke, I., Donahue, K. M., Davis, T. L. & Rosen, B. R. EPI imaging of global increase of brain MR signal with breath-hold preceded by breathing O2. Magn Reson Med 33, 448-52 (1995).

Edelman, R. R. et al. Qualitative mapping of cerebral blood flow and functional localization with echo-planar MR imaging and signal targeting with alternating radio frequency. Radiology 192, 513-20 (1994).

Detre, J. A. et al. Tissue specific perfusion imaging using arterial spin labeling. NMR Biomed 7, 75-82 (1994).

Alsop, D. C. & Detre, J. A. Reduced transit-time sensitivity in noninvasive magnetic resonance imaging of human cerebral blood flow. J Cereb Blood Flow Metab 16, 1236-49 (1996).

Detre, J. A. & Wang, J. Technical aspects and utility of fMRI using BOLD and ASL. Clin Neurophysiol 113, 621-34 (2002).

Buxton, R. B. Quantifying CBF with arterial spin labeling. J Magn Reson Imaging 22, 723-6 (2005).

* cited by examiner

Fig. 1 - Schematic of an exemplary PRAM scheme. The first row represents the PRS, the second the desired magnetization, the third and fourth the time step and image acquisitions, and the bottom row indicates when the 180° pulses must be applied to achieve the desired magnetization.

Fig. 2 - Schematic of exemplary PRS modulation of inflowing arterial spins.

Fig. 3 - Schematic of arterial magnetization during the PRS.

Fig. 4 - Relationship between exemplary PRAM inversion slab and imaged slice.

Fig. 5 - Reconstructed transit time distributions at 200 mL/min bulk flow. (a) TR = 50 ms; (b) TR = 100 ms.

Fig. 6 - Results of a tagging experiment on the flow phantom

Fig. 7 - Reconstructed exemplary transit time distributions at 100 mL/min bulk flow. TR = 100 ms.

Fig. 8 - PRAM images of mouse brain at TR=100ms. Transit times are indicated in each image. Acquired with: (a) Flip Angle = 45; (b) Flip Angle = 90.

Fig. 9 - Schematic of exemplary PRAM 180° pulse location

Fig. 10 - Schematic of PRAM 180° pulse location inside the phase encode loop.

COMPLEX AMPLITUDE MODULATION IN BLOOD FLOW AND PERFUSION MEASUREMENT FOR MEASURING A DISTRIBUTION OF TRANSIT TIMES ON A VOXEL BY VOXEL BASIS

CROSS REFERENCE TO RELATED APPLICATIONS

This application claims the benefit of U.S. Provisional Patent Application No. 60/781,501, entitled "METHODS OF MEASURING FLOW AND PERFUSION USING PSUEDO RANDOM AMPLITUDE MODULATION," filed on Mar. 9, 2006, the disclosure of which is hereby incorporated herein by reference.

TECHNICAL FIELD

The disclosed subject matter relates to medical imaging technology, and in particular to an improved method of measuring cerebral blood flow and perfusion using complex amplitude modulation schemes that allow for the resultant convolution of the distribution of transit times of the arterial blood with such modulation to be inverted by means of a Fourier analysis of the observed signal at a position of interest.

BACKGROUND

Cerebral blood flow ("CBF") is among the most important physiological variables in understanding local brain metabolism. CBF provides the physiological basis for blood oxygen level dependent (BOLD) contrast, the most frequently used imaging technique for estimating changes in neural activation[1] (all references cited to in this application are listed in Appendix A hereto, which is incorporated herein by reference). In addition to its fluctuations during normal brain function, CBF also changes during many of the pathological events that lead to acute or chronic brain dysfunction. Because these pathological changes typically have an earlier onset than structural biomarkers, measurement of CBF can be a useful tool in diagnosing stroke, ischemia, brain tumors, and dementia.

The earliest measurements of CBF used radioactive tracers.[2] In fact, positron emission tomography ("PET") measurements using radioisotopes such as $O^{15}$ are still regarded as the most accurate[3]. However, the invasiveness and expense of radioactive tracers significantly inhibit the widespread use of PET for CBF measurement.

Developments in MRI have led to an alternate method for measuring CBF, one using dynamic contrast enhancement following a rapid bolus injection of MR contrast agent. Although less invasive and expensive than radioactive tracers, this technique is still problematic, particularly in research settings. The need for venipuncture discourages some potential subjects, while others are excluded due to contraindications of the MRI contrast agent.

Arterial Spin Labeling ("ASL") techniques replace the need for an injected contrast agent by using water protons in the plasma as an endogenous MRI tracer. ASL is both non-invasive and cost effective, and has higher spatial resolution than PET. Additionally, its clinical utility is enhanced by the fact that ASL images can be routinely acquired during the same imaging session as structural or other MRI scans and can be directly compared with the anatomical and pathological features they reveal.

In ASL an endogenous tracer (arterial water) is used instead of an exogenous tracer. Flowing spins are inverted (labeled) at a plane in the main arteries which is proximal to an imaging volume. The labeled spins then flow through the arterial tree into the capillary bed arriving at a particular location in the tissue with a distribution of arrival or transit times. Once in the capillary bed, the arterial water molecules then exchange, one for one, with the extravascular water molecules. Due to the accumulation of inverted spins in the extravascular component of the tissue there is a reduction in the total magnetization of the tissue. This, in turn, causes a reduction in the imaged signal in that region of the imaged plane. The reduction in signal of the tissue in the imaged plane is thus proportional to the amount of labeled spin which flowed into that plane.

Using ASL, in general CBF can be measured by the subtraction of two images. The first is an unlabeled or control image in which there has been no inversion of the spins. The subsequent image is labeled, i.e., the spins have been inverted in an arterial plane proximal to the imaged slice. The resultant difference between the control and labeled images is directly proportional to the flow.

Two common methods of conducting ASL are Continuous ASL ("CASL") and Pulsed ASL ("PASL"). In PASL, spatially broad inversion pulses can be used to invert all of the spins in a region next to the slice of interest and the exchange between the inverted region and the imaged slice can be subsequently observed.[9] In most cases PASL measures the ratio of CBF at various locations because it is difficult to precisely define the amount of inflowing spins.

In CASL, incoming arterial water can be continuously inverted by an adiabatic inversion pulse. Although CASL can be used to measure CBF, this process is problematic in that it relies on certain assumptions regarding the transit times and the relative $T_1$'s of blood and tissue to do so. If an image is acquired rapidly following an RF irradiation the labeled arterial water will dominate the difference signal such that any signal reduction from the water molecules that have exchanged into the tissue will not be visible. While this can be addressed by imposing a post labeling delay (PLD), for this to be successful the PLD needs to be longer than the longest transit time. This tends to make PLD's long, which results in lesser signal detection inasmuch as the difference signal continually decreases as a function of PLD length.

In CASL, a separate acquisition is needed to obtain a control image. Flow can then be calculated from the difference between the control image and the labeled images. Transit times between the labeling and imaging planes are not measured in CASL. Nonetheless, transit time is an important parameter in the calculation of quantitative CBF.[14] To minimize the role of this unknown variable in flow quantification, post-labeling delays (PLD) between the end of labeling and the start of acquisition have been utilized, as noted. A PLD allows unlabeled spins which start flowing into the arterial tree sufficient time to wash out the labeled spins so that any labeled spins left in the arteries will not be confused with those that have exchanged into the tissue. Thus, if the PLD is longer than the transit time, the observed results are independent of transit time provided that the $T_1$'s in the blood and the tissue are the same, which is approximately true for gray matter. By varying a PLD one can investigate the effects of various transit times since an image acquired after a given PLD corresponds to integration over all longer transit times.[15]

However, the insertion of a PLD has several disadvantages. First, it is costly in SNR terms. Furthermore, it is vulnerable to changes in transit during activation as well as the potentially longer transit times that often occur in stroke and other cerebral vascular diseases (which can exceed the PLD). For example, a standard PLD sufficiently small not to degrade SNR beyond acceptable limits is 1 to 2 seconds, and the transit times common in stroke and other cerebral vascular diseases can be as large as 4 to 5 seconds.

In white matter, however, quantification of CBF using CASL encounters additional unique difficulties. The use of a PLD for measuring CBF in gray matter depends upon the assumption that the $T_{1gray}=T_{1blood}$, which, while acceptable for gray matter, is not valid for white matter. CASL also suffers from the lengthy transit time required for blood to reach white matter after being labeled in the artery. The relaxation of the labeled spins during this transit results in a much lower SNR for white matter relative to gray matter.

In ASL, the spins of protons in arterial water are typically inverted (labeled) at a plane in a cerebral artery. CBF then can be quantified by measuring the effect of the labeled spin when the protons enter a nearby imaging plane. However, when the transit time between the labeling and imaging planes cannot be measured, a major uncertainty is introduced into this calculation—it is difficult to discern how much of the detected signal is due to label accumulated in the tissue or label remaining in the arterial space in the tissue. While CASL attempts to reduce this uncertainty by introducing a PLD between the end of the labeling pulse and the start of data acquisition, this solution is only partially effective; there is uncertainty regarding the relative relaxation times, and it imposes an approximately three-fold cost in signal-to-noise ratio due to the longitudinal relaxation of the label during the PLD interval.

Moreover, current ASL methods use a continuous or square waveform for spin labeling. This can be difficult for the RF amplifiers on most commercial MR scanners to generate because they are generally designed for pulsed, as opposed to continuous, applications.

Finally, CASL uses lengthy (e.g., 1-2 second) RF pulses for spin labeling. The length of such pulses tends to place strain on the RF transmitters in most MRI scanners that is typically relieved through the use of transmit-receive head coils. However, receive-only coils offer greater sensitivity and are more widely available making this solution non-optimal. Additionally, long RF pulses introduce confounds from magnetization transfer (MT) effects whereby the spins in the imaged plane are saturated by the long RF pulse. To address this, CASL requires that the acquisition of a control image be done in the presence of a RF pulse which mimics the MT effects of labeled images but does not invert the arterial spins. However, while this approach eliminates MT effects, it introduces additional sources of error, particularly motion artifacts.

Thus, what is needed in the art is a method of blood flow and perfusion measurement that can overcome the problems of conventional methods, and that can allow for the direct measurement of transit time distribution while acquiring ASL data.

What is further needed in the art is a method of blood flow and perfusion measurement that can add certainty to CBF quantification and obviate the need for PLD's control image acquisition or reliance on less sensitive signal receiving hardware.

SUMMARY

Systems and methods for blood flow and perfusion measurement using complex amplitude modulation of MRI pulses are presented. In exemplary embodiments of the disclosed subject matter, inflowing arterial spins can be modulated using a "complex" modulation function having defined mathematical properties in the frequency domain, such as, for example, a pseudo-random sequence. In exemplary embodiments of the disclosed subject matter such complex modulation functions can be used to measure individual transit times by deconvolving them from a series of acquired images. In exemplary embodiments of the disclosed subject matter images can be acquired at the same rapid rate as arterial modulation, and transit time distribution in the imaged tissue can be determined as part of a single integrated acquisition.

DETAILED DESCRIPTION

Figure 1:
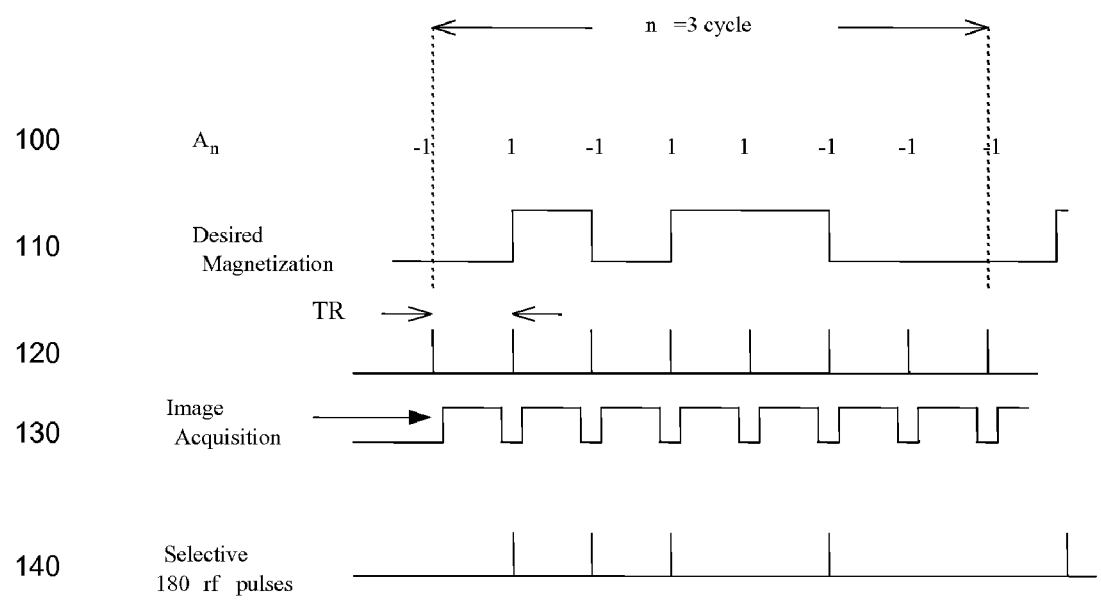
FIG. 1 is a schematic representation of a pseudo-random amplitude modulation scheme according to an exemplary embodiment of the disclosed subject matter.

Since their introduction in the 1990's,[4,5,6] arterial spin labeling ("ASL") techniques have proven to be very useful in acquiring absolute and relative CBF measures, as well as regional perfusion data in a wide variety of circumstances.[7] ASL techniques replace the need for an injected contrast agent by using water protons in the plasma as an endogenous MRI tracer. ASL is both non-invasive and cost effective, and has higher spatial resolution than PET. Additionally, its clinical utility is enhanced by the fact that ASL images can be routinely acquired during the same imaging session as structural or other MRI scans and can be directly compared with the anatomical and pathological features they reveal.

In ASL an endogenous tracer (arterial water) is used instead of an exogenous tracer. Flowing spins are inverted (labeled) at a plane in the main arteries which is proximal to an imaging volume. The labeled spins then flow through the arterial tree into the capillary bed arriving at a particular location in the tissue with a distribution of arrival or transit times. Once in the capillary bed, the arterial water molecules then exchange, one for one, with the extravascular water molecules at a rate given by KS, where K is the local permeation and S is the surface area of the capillary bed. Due to the accumulation of inverted spins in the extravascular component of the tissue there is a reduction in the total magnetization of the tissue. This, in turn, causes a reduction in the imaged signal in that region of the imaged plane. The reduction in signal of the tissue in the imaged plane is thus proportional to the amount of labeled spin which flowed into that plane.

In general, CBF can be measured by the subtraction of two images. The first is an unlabeled or control image in which there has been no inversion of the spins. The subsequent image is labeled, i.e., the spins have been inverted in an arterial plane proximal to the imaged slice. The resultant difference between the control and labeled images is directly proportional to the flow. If the inversion is modulated in time[8] then the signal from the labeled spins flowing into the imaged slice is the convolution of the modulation function and the distribution of the transit times. This occurs because the observed signal at the imaged slice is the sum of static spins in the imaged plane together with those brought to the imaged slice by the flow of the blood and its perfusion into the tissue in the imaged slice. Each element of the sum is modulated by the amplitude of the modulation scheme employed to label the inflowing arterial blood. This sum is known as a convolution and can be inverted to recover the distribution of the arterial transit times to the imaged slice from the location of their inversion. This can be described mathematically, for example, using the following equation:

$$S(\vec{r}, t) = \int_0^\infty A(\tau) f(\vec{r}, t - \tau) d\tau$$

where S is the signal, A is the arterial modulation as a function of time and f is the distribution of transit times.

As noted, two common methods of conducting ASL are continuous ASL (CASL) and pulsed ASL (PASL). In CASL, incoming arterial water is continuously inverted by an adiabatic inversion pulse. This pulse can be created by the passage of the moving spins through a resonance condition created by a continuous RF waveform that irradiates the artery in the presence of a gradient.[4] Although CASL can be used to measure CBF, this process relies on certain assumptions regarding the transit times and the relative $T_1$'s of blood and tissue to do so. As described in greater detail below, if an image is acquired rapidly following an RF irradiation the labeled arterial water will dominate the difference signal such that any signal reduction from the water molecules that have exchanged into the tissue will not be visible. This can be addressed, for example, by imposing a post labeling delay (PLD) between the end of the RF irradiation and the acquisition of the image. For this to be successful, however, the PLD needs to be longer than the longest transit time. This tends to make PLD's long, which results in lesser signal detection inasmuch as the difference signal continually decreases as a function of PLD length.

In PASL spatially broad inversion pulses can be used to invert all of the spins in a region next to the slice of interest and the exchange between the inverted region and the imaged slice can be subsequently observed.[9] Details of how the inversions are done can, in general, vary considerably.[5,10-12] In most cases PASL measures the ratio of CBF at various locations because it is difficult to precisely define the amount of inflowing spins. Recently, sequences have been developed that can address this problem[13] by the addition of a separate RF pulse to saturate inflowing spins after a certain time. Assuming a square rectangular input to the imaged plane, these sequences can also be used can measure absolute CBF using similar assumptions as are made for CASL, as described above.

In standard CASL, a continuous RF waveform of resonant offset $f_0$ in the presence of a gradient is used to invert all inflowing spins. The inversion is achieved through an effective adiabatic pulse seen by the spins at the inversion plane $z_0(f_0 = yG\ z_0)$, since they pass from far below, through, and then above resonance as they move along the artery. The inverted spins then flow through an arterial tree and, after a transit time to reach the imaging plane, exchange with the tissue water. This method assumes that water is a freely diffusible tracer, which is a reasonable assumption at most flow rates. The inversion pulse is generally left on for several seconds to ensure that the steady state of magnetization is reached prior to image acquisition.

In CASL, a separate acquisition is needed to obtain a control image. Flow can then be calculated from the difference between the control image and the labeled images. In general, the differences observed between labeled images and control images are on the order of 1%, which, although small, can be measured by averaging over several periods of label and control. One confound in this calculation is that the relatively long off-resonance continuous RF pulse used for labeling the spins can create magnetization transfer (MT) effects. These effects result from chemical exchange between protons in proteins and lipids and protons in water, altering the characteristics of the labeled images by lowering the overall signal. Consequently, subtracting a control image (absence of RF) from a labeled image (presence of RF) includes MT effects in addition to the desired flow information. Thus, the difference image in such a case appears to be more different than it should be due to the movement of the inverted spins into the imaged slice.

To circumvent this problem, a cosine amplitude modulation can be introduced in the continuous waveform and applied during the acquisition of the control image.[14,15] Such a modulation creates two closely spaced adiabatic inversion planes in the inflowing arterial spins so that there is no net inversion. However, because the power levels of the RF waveforms for the control image and label image are adjusted to be equal, they induce similar MT effects in both. As a result these effects are theoretically cancelled during the subtraction.

Transit times between the labeling and imaging planes are not measured in CASL. Nonetheless, transit time is an important parameter in the calculation of quantitative CBF.[14] As noted above, to minimize the role of this unknown variable in flow quantification, post-labeling delays (PLD) between the end of labeling and the start of acquisition can be utilized. A PLD allows unlabeled spins which start flowing into the arterial tree sufficient time to wash out the labeled spins so that any labeled spins left in the arteries will not be confused with those that have exchanged into the tissue. Thus, if the PLD is longer than the transit time, the observed results are independent of transit time provided that the $T_1$'s in the blood and the tissue are the same, which is approximately true for gray matter. By varying a PLD one can investigate the effects of various transit times since an image acquired after a given PLD corresponds to integration over all longer transit times.[15]

Although the insertion of a PLD makes it possible for CASL to quantify CBF without a priori knowledge of transit times, this solution has several disadvantages. First, it is costly in SNR terms. Furthermore, it is vulnerable to changes in transit during activation as well as the potentially longer transit times that often occur in stroke and other cerebral vascular diseases (which can exceed the PLD). For example, a standard PLD sufficiently small not to degrade SNR beyond acceptable limits is 1-2 seconds, and the transit times common in stroke and other cerebral vascular diseases can be as large as 4 to 5 seconds.

In white matter, however, quantification of CBF using CASL encounters unique difficulties. The use of a PLD for measuring CBF in gray matter depends upon the assumption that the $T_{1gray}=T_{1blood}$, which, while acceptable for gray matter, is not valid for white matter. CASL also suffers from the lengthy transit time required for blood to reach white matter after being labeled in the artery. The relaxation of the labeled spins during this transit results in a much lower SNR for white matter relative to gray matter.

As noted, CASL is a widely used technique for the measurement of cerebral blood flow and brain perfusion in magnetic resonance imaging ("MRI"). Such measurement is clinically significant because alterations in CBF occur early in many pathologies including stroke, tumor, ischemia, and dementia. Compared to other techniques for CBF imaging, CASL is non-invasive, inexpensive, and provides high-resolution images. It can also provide absolute quantification of CBF, but this potential is rarely utilized due to the limitations of current methods as described below.

In ASL, the spins of protons in arterial water are typically inverted (labeled) at a plane in a cerebral artery. CBF then can be quantified by measuring the effect of the labeled spin when the protons enter a nearby imaging plane. As noted above, when the transit time between the labeling and imaging planes cannot be measured, a major uncertainty is introduced into this calculation—it is difficult to discern how much of the detected signal is due to label accumulated in the tissue or label remaining in the arterial space in the tissue. CASL reduces this uncertainty by introducing a post labeling delay (PLD) between the end of the labeling pulse and the start of data acquisition, provided the PLD is longer than the longest transit time and the relaxation times in the tissue are similar to those in the artery. This means the signal is dominated by spins in the tissue rather than the arteries. However, this solution is only partially effective; there is uncertainty regarding the relative relaxation times, and it imposes an approximately three-fold cost in signal-to-noise ratio due to the longitudinal relaxation of the label during the PLD interval.

Moreover, current ASL methods use a continuous or square waveform for spin labeling. This can be difficult for the RF amplifiers on most commercial MR scanners to generate because they are generally designed for pulsed, as opposed to continuous, applications.

Finally, CASL uses lengthy (e.g., 1-2 second) RF pulses for spin labeling. The length of such pulses tends to place strain on the RF transmitters in most MRI scanners that is typically relieved through the use of transmit-receive head coils. However, receive-only coils offer greater sensitivity and are more widely available making this solution non-optimal. Additionally, long RF pulses introduce confounds from magnetization transfer (MT) effects whereby the spins in the imaged plane are saturated by the long RF pulse. To address this, CASL requires that the acquisition of a control image be done in the presence of a RF pulse which mimics the MT effects of labeled images but does not invert the arterial spins. However, while this approach eliminates MT effects, it introduces additional sources of error, particularly motion artifacts.

CASL is currently the leading method for measuring CBF because it is non-invasive, inexpensive, and compatible with anatomical and functional MRI images acquired during the same scanning session. However, as noted, CASL is unable to measure transit times directly.

As noted above, while CASL can quantify CBF by introducing a PLD, such a solution is only partially effective for gray matter and less so for white matter. This is because the relaxation times in gray matter are closer to those of arterial water than those of white matter. Further, because the transit times are longer for white matter than for gray matter, the larger difference in relaxation times is further amplified. Furthermore, a PLD reduces SNR and introduces confounds from MT. Additionally, because CASL cannot distinguish the effects of transit time from the measurement of flow, although it may detect a change, it cannot distinguish the source of that change. As it is widely recognized that some processes of interest, such as, for example, neural activation and stroke, may involve alterations of transit times as well as flow, this is a significant limitation.

Thus, in conventional ASL there is an absence of information regarding transit time distribution. In exemplary embodiments of the disclosed subject matter transit time distribution can be measured while acquiring ASL data. This can be done, for example, by modulating the arterial input with a "complex" modulation function, i.e., a function having certain properties in the frequency domain that allow the resultant convolution of the distribution of transit times of the arterial blood with the complex modulation to be inverted by means of a Fourier analysis of the observed signal at the position of interest. This requires a modulation scheme whose Fourier transform has no zeros. A common example of such a complex modulation scheme is a pseudo random sequence or "PRS."

To illustrate such methods, an analysis of how the effects of the transit time are incorporated into an acquired signal is next described.

As noted above, mathematically, a transit time distribution enters as its convolution with the arterial input modulation function. I.e., the signal at each voxel is the integral of all of the spins from all of the different transit times that traveled from the inversion plane to that voxel. This can be expressed, for example, as $$\Delta I(\vec{r}, t) = \int_0^\infty A(t-\tau) f(\vec{r}, \tau) d\tau \qquad \text{(Eq. A)}$$

where $\Delta I$ is the change in image intensity observed at a specific point and time due to the inflowing spins, $A(t-\tau)$ is the arterial spin amplitude modulation at the inversion plane at time $t-\tau$, and $f(\vec{r},\tau)$ is the fraction of spins in a voxel that take $\tau$ time units to travel from the edge of the inversion slab to that voxel. It is noted that this equation has been simplified by assuming that $T_1$ is infinite in order to illustrate the effects of varying the arterial input function. This assumption has the effect of ignoring any relaxation as the arterial spins travel from the inversion plane to the imaging plane. A more detailed description is provided below.

Barbier et al.[8,16] have proposed a modulation scheme that is a square wave of various frequencies which allow the time response of the perfusion to be mapped out. By acquiring images at different modulation frequencies, the transit time dependence of the process can be measured. Thus, in the Barbier method $A(t-\tau)$ is a square wave of varying frequencies. In standard CASL the input function is a constant −1, but due to waiting for a PLD delay time the effective signal is $\int_{PLD}^{\infty} A(t-\tau)f(\vec{r},\tau)d\tau$, where the lower limit of the integral has been increased to the PLD inasmuch as subtraction of the control image eliminates contributions from times shorter than the PLD.

To follow the motion of blood as it makes its way from a labeling site to an imaging plane through an arterial tree, it is desirable to know the arterial transit time distribution function $f(\vec{r},\tau)$, at each point in space and time. Theoretically, perhaps the simplest way to do this is to invert a narrow band at the labeling site and then observe those spins as they pass through an arterial tree and exchange into tissue across the capillary walls. In such case evaluating the convolution result is simple inasmuch as the arterial modulation function is effectively a delta function in time, $A(t)=M_0\delta(t_0)$, and thus $I(\vec{r},t)=M_0 f(\vec{r},t-t_0)$. This essentially states that a narrow inversion through an arterial system can be followed into the parenchyma, imaging it as it goes. In this way transit times and accumulation in the parenchyma of the labeled spins in a series of sequential images can be measured. In practice, however, such a method does not work due to the fact that as the labeling gets narrower intensity is lost and the duty cycle of the label becomes very small.

Thus, an alternative function for A is needed that can allow for solution of the equation in real-world contexts. The nature of alternative A's can be seen by recalling that if the Fourier transform of a convolution of two functions is taken, the product of the Fourier transforms is obtained. Thus, if I=A conv. f, then $FT\{I\}=FT\{A \text{ conv. } f\}=FT\{A\}*FT\{f\}$, and
$FT\{f\}=FT\{I\}/FT\{A\}$.

This fact makes the equation easy to solve for f, provided that there are no zeros in the Fourier transform of A. In fact, this is why the delta function works—it has unit amplitude everywhere in Fourier space. As is known, any function with unit amplitude in Fourier space must, by Parseval's theorem, have a delta function as its autocorrelation function. What is therefore sought is a function that has no correlation with itself over time, i.e., one that has a randomly modulated series of 1's and −1's. One example of such a series is known as "pseudo-random" (also a maximum length) series because it resembles an uncorrelated random series. However, since it has finite length, it cannot be truly random and is thus termed "pseudo-random". It is easy to generate pseudo-random sequences of length $2^n-1$ because they can be, for example, generated by linear shift registers based on prime binary polynomials.[17] If it is assumed to be such a sequence, then $$\sum_{j=0}^{N-1} A_j A_{y-k} = (N+1)\delta_{ok} - 1 \text{ where } N = 2^n - 1.$$

In this expression the −1 comes from the fact that the number of elements in the sequence is odd and thus cannot exactly cancel.

In exemplary embodiments of the disclosed subject matter these concepts can be extended by modulating arterial spins with a complex function that satisfies these mathematical conditions. As noted above, a pseudo-random sequence (PRS) is an example of such a complex function, and exemplary embodiments of the disclosed subject matter using a PRS will be described in what follows. The extension to other complex modulation functions is easily implemented as will be understood by those skilled in the art. Such a modulation sequence can allow, for example, for the transit time distribution to be deconvolved from the acquired image. Thus, expressed in the form of an equation, and assuming a PRS, the following can be obtained:

$$\Delta I(\vec{r}, t_k) = \int_0^\infty A(t_k - t_j) f(\vec{r}, t_j) dt_j = \sum_{j=0}^{2^n-1} A_{k-j} f(\vec{r}, t_j)$$

$$\sum_{k=0}^{2^n-1} A_{k-l} \Delta I(\vec{r}, t_k) = \sum_{k=0}^{2^n-1} A_{k-l} \sum_{j=0}^{2^n-1} A_{k-j} f(\vec{r}, t_j)$$

$$= \sum_{j=0}^{2^n-1} \left( \sum_{k=0}^{2^n-1} A_{k-l} A_{k-j} \right) f(\vec{r}, t_j)$$

$$= \sum_{j=0}^{2^n-1} \{(2^n - 1)\delta_{lj} - 1\} f(\vec{r}, t_j) \approx (2^n - 1) f(\vec{r}, t_l)$$

(hereinafter the "Deconvolution Equation").

In exemplary embodiments of the disclosed subject matter, arterial labeling with a PRS can thus offer the advantages of CASL while eliminating the problems associated with the introduction of a PLD.

In exemplary embodiments of the disclosed subject matter, an arterial input function can be modulated with a PRS by applying a series of broad slice selective 180° RF pulses which inverts the spins in the entire region between the chosen input artery of interest and the region of the brain containing the imaged slice or slices of interest. The edge of the selective slice can be, for example, at a desired inversion plane and the width of the slice can be, for example, large enough to include the imaging plane as well. The presence or absence of an inversion pulse can be determined by the elements of the PRS, with a 180° pulse applied whenever the PRS changes sign, as shown, for example, in FIGS. 1 and 2 (rows 140 in FIG. 1, and 250 in FIG. 2, respectively show the occurrence of selective 180° pulses). This results in the longitudinal magnetization of incoming arterial spins to be modulated to be equal to the PRS.

In exemplary embodiments of the disclosed subject matter, the time between elements in such a series can be set to 100-200 ms so as to be sufficiently short in comparison with variations in the transit time distribution of approximately ~1-2 seconds. Thus, in exemplary embodiments of the disclosed subject matter, a PRS can, for example, be cycled through at one element per TR. Thus, during each TR period new inflowing spins can cross the inversion plane and can be inverted or not according to the PRS modulation scheme.

In exemplary embodiments of the disclosed subject matter, an imaged slice can be sampled every TR. Assuming that a PRS has been exactly replicated, turning the original convolution integral (Eq. A above) into a sum gives the following expression for the signal due to inflowing spins:

$$\Delta I(\vec{r}, t_n) = \sum_{j=0}^{N-1} A_{n-j} f(\vec{r}, t_j) \text{ where } t_n = n \cdot TR.$$

To invert this $\Delta I(\vec{r}, t_n)$ can be multiplied by a shifted $A_n$, as follows:

$$\Delta S(\vec{r}, t_k) = \sum_{l=0}^{N-1} A_{k-l} \Delta I(\vec{r}, t_l) = \sum_{l=0}^{N-1} A_{k-l} \sum_{j=0}^{N-1} A_{l-j} f(\vec{r}, t_j)$$

$$= \sum_{j=0}^{N-1} f(\vec{r}, t_j) \sum_{l=0}^{N-1} A_{k-l} A_{l-j} = \sum_{j=0}^{N-1} f(\vec{r}, t_j) \sum_{m=k}^{k-N+1} A_m A_{k-j-m}$$

$$= \sum_{j=0}^{N-1} f(\vec{r}, t_j)((N+1)\delta_{0k-j} - 1) = (N+1)f(\vec{r}, t_k) -$$

$$\sum_{j=0}^{N-1} f(\vec{r}, t_j) = (N+1) \left( f(\vec{r}, t_k) - \frac{\langle f(\vec{r}) \rangle}{N+1} \right)$$

where $\langle f(\vec{r}) \rangle = \sum_{j=0}^{N-1} f(\vec{r}, t_j)$.

It is noted that $$\sum_{j=0}^{N-1} \Delta S(\vec{r}, t_j) = (N+1) \sum_{j=0}^{N-1} \left( f(\vec{r}, t_k) - \frac{\langle f(\vec{r}) \rangle}{N+1} \right) =$$

$$(N+1) \left( \langle f(\vec{r}) \rangle - \frac{\langle f(\vec{r}) \rangle}{N+1} \right) = N \langle f(\vec{r}) \rangle.$$

This allows for the recovery of the desired distribution function except for a small correction due to the average transit time image $\langle f(\vec{r}) \rangle$, given by the two previous equations which can be easily removed as a simple offset. In exemplary embodiments of the disclosed subject matter, this offset can be calculated, for example, by summing the $\Delta S$'s over the transit times. The images can then, for example, be deconvolved with the input function to recover the images of the transit time distribution.

Thus, in exemplary embodiments of the disclosed subject matter, such processing can effectively create images that are "snapshots" of where the spins have traveled to at that particular transit time.

In exemplary embodiments of the disclosed subject matter, by modulating arterial spins with a such a complex sequence, such as, for example, a PRS, all of the advantages of CASL can be obtained without any of its drawbacks. Pseudo-random Amplitude Modulation ("PRAM") can offer both non-invasive quantification of CBF as well as measurement of transit times. This is possible because PRAM modulates the spins flowing across the labeling plane according to a pseudo-random sequence. Subject to $T_1$ recovery, the mathematical properties of this modulation of the longitudinal magnetization in the arterial spins allow for measurement of all the transit times present in imaged tissue as part of a single integrated acquisition.

FIG. 1 schematically illustrates an exemplary modulation scheme $A_n$ 100 with a PRS of length 7 ($L=2^n-1=3$), according to an exemplary embodiment of the disclosed subject matter. The desired magnetization 110 is shown in the second row of the figure, a clock step TR 120 in the third row and an image acquisition block 130 in the fourth row. In exemplary embodiments of the disclosed subject matter, to achieve the desired modulation of the incoming spins selective 180° pulses can, for example, be applied as indicated in the bottom row 140 of FIG. 1. As can be seen in FIG. 1, they occur each time the PRS changes sign. In this example, the entire sequence repeats after 7 steps, and in general a PRS repeats after $2^n-1$ steps.

Figure 2:
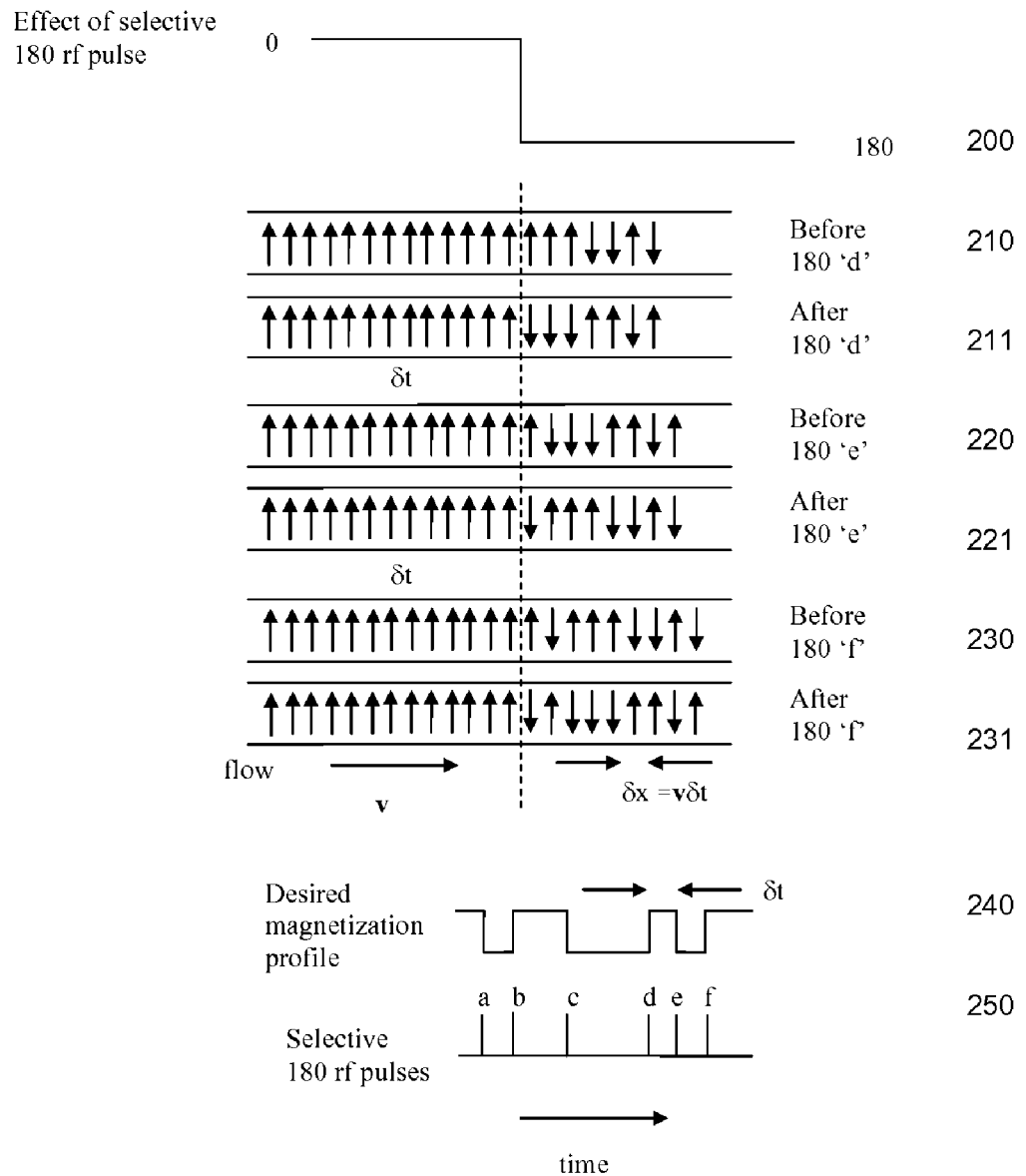
FIG. 2 is a schematic representation of pseudo-random sequence modulation of inflowing arterial spins according to an exemplary embodiment of the disclosed subject matter.

The effect of such a series of 180° pulses is schematically illustrated in FIG. 2 for block flow in a tube. With reference thereto, top row 200 illustrates the edge of a selective 180° pulse, while the bottom two rows show the desired magnetization profile 240, and the locations of the selective 180° pulses 250, respectively. Middle rows 210, 211, 220, 221 and 230, 231 illustrate the effect of the RF pulses. In the example shown in FIG. 2, spins are flowing from left to right at velocity v, and are therefore moving a distance $\Delta x = v \Delta t$ ($\Delta t = TR$) between clock pulses. The spin distribution before pulse 'd' 210 shows a magnetization pattern of $-1,1,-1,-1,1,1,1$ (reading from right to left) which is what is expected after pulses 'a', 'b' and 'c' have been applied. Thus, the effect of pulse 'd' is simply to invert the existing distribution as shown in 211. In the next $\Delta t$ more spins flow into the inversion slab, as shown in row 220, and are then inverted after pulse 'e' as shown in row 221. This also occurs between pulses 'e' and 'f', as shown in rows 230 and 231, respectively, leading to the final distribution which is the desired magnetization. It is noted that the rightmost spins in FIG. 2 will appear at the earliest times and thus are apparently reversed with respect to the magnetization profile given in the figure.

A detailed theoretical analysis of the concepts underlying the disclosed subject matter is next provided. To summarize, in exemplary embodiments of the disclosed subject matter a sequence such as a PRS can be used to create a complex modulation of an input function at an inversion plane. This modulation can be determined by the chosen sequence and can be implemented in the longitudinal magnetization of the arterial spins. These labeled spins can, for example, then travel to the imaged slice, lose their label at the arterial $T_{a1}$, and exchange into the parenchyma through the capillaries. It is assumed here that all spins exchange (using the known well mixed tissue assumption) and only leave the tissue through the venous drainage at the rate set by the CBF. To analyze the effects of the PRS it can be assumed that $TR \ll T_1$, and the modified Bloch equations can be linearized so that the magnetization can be expressed in terms of the elements of the PRS, $\{A_n\}$.

As detailed below, there are two types of signals observed in the imaged slice—those that come from the static spins in the slice and those that come from the spins that exchange into the tissue from the capillaries. The signal from the static spins appears to have zero transit time and decays with the combined effects of the tissue $T_1$, the CBF and the effects of the excitation pulse. The signal from the exchanged spins appears in the tissue after its transit time and subsequently decays at the same rate as the static spins.

In what follows, the modulation of inflowing arterial spins caused by the selective 180° pulses as controlled by a PRS is first analyzed. Next, the effects of the sequence of 180° pulses on the spins at the imaged slice, both static and flowing, are analyzed. In all cases it is assumed that a PRS is initially repeated once to prepare the system so that the first pulse is not unique and the system is a steady state with respect to the pseudo-random excitations. This means that sequence $\{A_n\}$, is cyclical and that the index should always be the calculated modulus of its length. It is understood that if a different complex modulation scheme were employed then the detailed autocorrelation function of such employed modulation scheme would be used instead of that for a PRS.

To analyze the arterial input that appears at the tissue, it is necessary to take into account all of the 180° pulses that the flowing spins experience. The magnetization that arrives at the imaged slice is thus a sum of the different transit times (due to different paths or velocities) from the edge of the inversion slab to the slice location (subjected, of course, to any T1 relaxation that has occurred in the interval). At every TR the arterial spins that have crossed into the inversion slab will or will not experience a 180° pulse as determined by the PRS elements. Exactly how many of these they will experience depends on how long it takes them to travel to the slice location. For each transit time the arterial spins can be modulated differently by the effects of the PRS. If the effects of relaxation are initially ignored then the equation relating the arterial longitudinal magnetization and the flow distribution can be stated, for example, as $$M_i = \sum_{j=0}^{N-1} M^0 (-1)^{\sum_{k=i}^{i-j} S_k} f_j, \quad [1]$$

where $M_i$ is the image observed at the $i^{th}$ element in the PRS, $f_j$ is the spins that have taken j TR periods to move from the edge of the inversion slab to the slice location, and $S_k$ is either 0 or 1 depending on whether there had been a 180° pulse at the $k^{th}$ step of the PRS.

Figure 3:
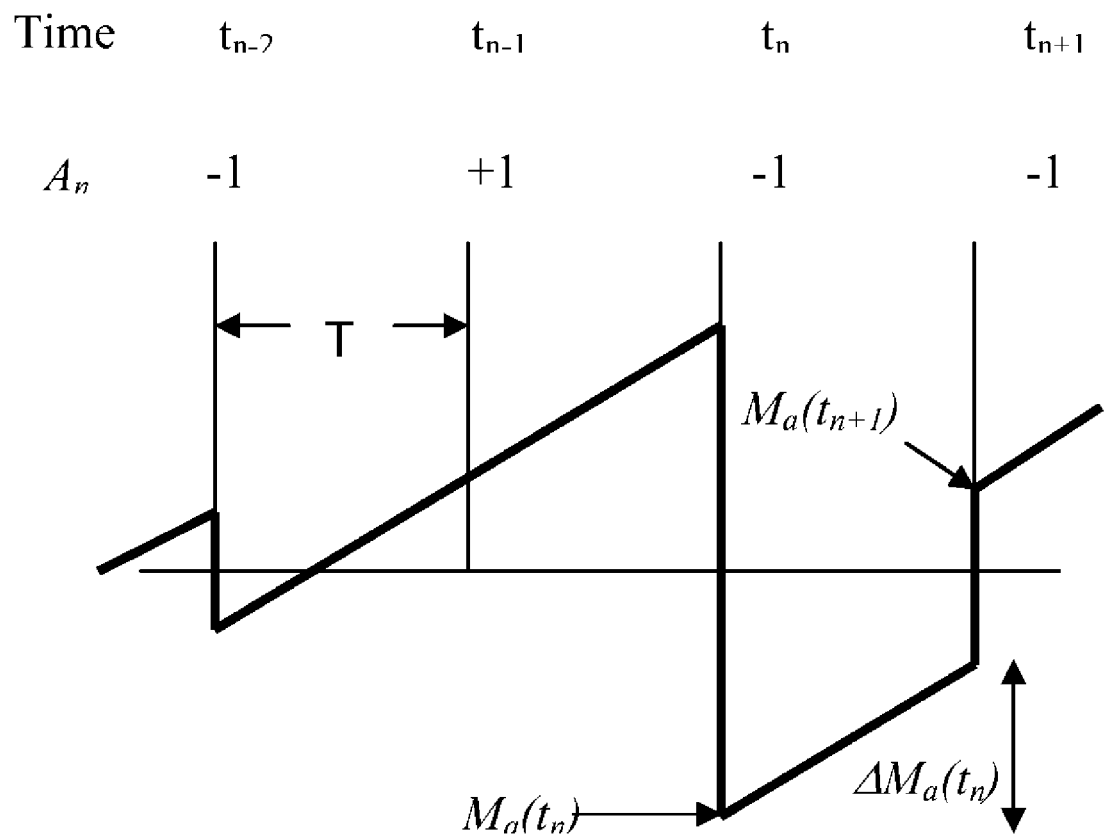
FIG. 3 is a schematic representation of arterial magnetization during an exemplary pseudo-random sequence according to an exemplary embodiment of the disclosed subject matter.

To extend this analysis to take into account the relaxation of the label, the Bloch equation, $$\frac{dM_a(t)}{dt} = \frac{M_a^0 - M_a}{T_{a1}},$$

can be combined with the effects of the 180° pulses from the PRS sequence. Because of the variability of a PRS it is generally necessary to consider the effect of each 180° pulse separately. This can be done, for example, by linearizing the Bloch equation (since TR<<$T_{a1}$), and calculating the effects of each pulse recursively. FIG. 3 depicts an exemplary evolution of arterial magnetization $M_a$ from $t_{n-2}$ to $t_{n+1}$ under the effects of the PRS $\{A_n\}$ according to an exemplary embodiment of the disclosed subject matter. Mathematically, a recursive relationship can be developed for the arterial magnetization at time $t_n$ in terms of a sum over variable transit times as follows, assuming there is no stimulated echo formation which can be prevented by RF phase cycling in the PSR:

$$M_a(t_{n+1}) = (M_a(t_n) + \Delta M_a(t_n))(-1)^{S_n} \quad [2]$$

$$\Delta M_a(t_n) = \frac{M^0 - M_a(t_n)}{T_{a1}} TR$$

$$M_a(t_{n+1}) = [M^0 \delta + M_a(t_n)(1-\delta_a)](-1)^{S_n} \text{ where } \delta_a = \frac{TR}{T_{a1}}$$

$$= [M^0 \delta_a +$$

$$[M^0 \delta_a + M_a(t_{n-1})(1-\delta_a)](-1)^{S_{n-1}}(1-\delta_a)](-1)^{S_n}$$

$$= [M^0 \delta_a + [M^0 \delta_a + [M^0 \delta_a +$$

$$M_a(t_{n-2})(1-\delta_a)](-1)^{S_{n-2}}(1-\delta_a)](-1)^{S_{n-1}}(1-\delta_a)](-1)^{S_n}$$

$$= M^0 \delta_a (-1)^{S_n} [1 + (-1)^{S_{n-1}}(1-\delta_a)\{1 + (-1)^{S_{n-2}}(1-\delta_a)\}] +$$

$$M_a(t_{n-2})(1-\delta_a)^3 (-1)^{S_{n-2}-S_{n-1}-S_n}$$

so, in general, for a transit time of lΓTR the following relationship between the magnetization at $t_{n-1}$ results:

$$M_a(t_{n+1}) =$$

$$M_a(t_{n-l})(1-\delta_a)^{l-1}(-1)^{\sum_{j=0}^{l} S_{n-j}} + M^0 \delta_a \sum_{i=0}^{l}(1-\delta_a)^i (-1)^{\sum_{j=0}^{i} S_{n-j}}$$

As noted above, $S_n$ is cyclic. Thus n is the calculated modulus with respect to the PRS period, N. The first term in equation [2] comes from spins which have moved from the inversion plane to the imaging plane. The second term is a sum of all of the ΔM's accumulated in the lTR intervals that the blood experienced as it traveled to the imaging plane, each being modulated by the PRS pulses that occurred in the ensuing time.

Further, $(1-\delta_a)^i \approx \exp(-i\delta_a) =$ $$\exp\left(-\frac{iTR}{T_{a1}}\right) = \exp\left(-\frac{t_i}{T_{a1}}\right) \text{ since } \exp(-x) = \lim_{l \to \infty}\left(1 - \frac{x}{i}\right)^i \Phi$$

Thus, this equation reproduces the expected $T_{a1}$ decay of the label as it travels through the arterial tree.

To convert this analysis to transit times, $f(t_j)$ is set to represent the fraction of arterial magnetization that takes $t_j$ to travel from the inversion plane to the imaging plane. The sum of $f(t_j)$ over all transit times is 1. The arterial magnetization at $t_{n+1}$ is thus simply the sum of the contributions from prior times multiplied by their fractional contribution, which is given by f.

$$M_a(t_{n+1}) = \sum_{k=0}^{N_f} f(t_k) \left\{ M_a(t_{n-k})(1-\delta_a)^{k+1}(-1)^{\sum_{j=0}^{k} S_{n-j}} + \right. \quad [3]$$

$$\left. M^0 \delta_a \sum_{i=0}^{k}(1-\delta_a)^i (-1)^{\sum_{j=0}^{i} S_{n-j}} \right\}$$

where $N_f$ is the maximum transit time (in TR's)

$$= \sum_{k=0}^{N_f} f(t_k) M^0 \left\{ (1-\delta_a)^{k+1}(-1)^{\sum_{j=0}^{k} S_{n-j}} + \delta_a \sum_{i=0}^{k}(1-\delta_a)^i (-1)^{\sum_{j=0}^{i} S_{n-j}} \right\}$$

or, readjusting the subscripts slightly $$M_a(t_n) = M^0 \sum_{k=0}^{N_f} P_{n,k}(1-\delta_a)^{k-1} f(t_k) = M^0 Pg, \text{ where}$$

$$P_{n,k} = (-1)^{\sum_{j=0}^{k} S_{n-j-1}} + \delta_a \sum_{i=0}^{k}(1-\delta_a)^{i-k-1}(-1)^{\sum_{j=0}^{i} S_{n-j-1}},$$

$$g_k = (1-\delta_a)^{k+1} f(t_k).$$

The step from the first to the second lines above follows as $M_a(t_{n-k})$ equals $M^0$ because that group of spins crossed the inversion plane at $t_{n-k}$ and is therefore then at their equilibrium magnetization. It is noted that the first part of the expression in [3] in the brackets is similar to equation [1]. In fact, in the limit as Δ→0, corresponding to an infinite $T_{a1}$, the expressions are the same. For TR<<$T_{a1}$ the second term in $P_{n,k}$ can be ignored in comparison with the second term. Using this expression P can be calculated and inverted to get $P^{-1}$ which can, for example, then be used to solve the equation for f. Using this calculus transit time images for both example flow phantoms and a mouse brain were calculated, as described below.

The analysis can similarly be extended, for example, to perfused tissue in the imaged slice. In this case the situation is more complex because the effects of the excitation pulse have to be addressed and the fact that the arterial spins are exchanging into the tissue needs to be taken into account. As is known, the Kety-Schmidt equation describes the exchange of water into tissue as given below in equation [4]. This assumes that water is a freely diffusible tracer and that the tissue can be described as a single, well mixed solution.[18]

$$\frac{dM_t}{dt} = \frac{M_t^0 - M_t}{T_{t1}} + CBF\left\{M_a - \frac{M_t}{\lambda}\right\} = \frac{M_t^0}{T_{t1}} - M_t\left(\frac{1}{T_{t1}} - \frac{CBF}{\lambda}\right) + CBF \cdot M_a \quad [4]$$

where $M_t$ is the tissue magnetization, $M_t^0$ its equilibrium value, $T_{t1}$ its longitudinal relaxation time, CBF the cerebral blood flow and $\lambda$ the blood brain partition coefficient. It is noted that CBF is really a function of position.

It is further noted that the relaxation time $T_{t1}$ is much shorter (~1 sec) than the exchange lifetime CBF/$\Delta$(~100 sec); thus, the relaxation time is the dominant pathway for the label to disappear.

To further analyze this equation, a similar linearizing approach can be used, for example, inasmuch as TR<<$T_1$. Also, the effects of the excitation pulse on the spins, assumed to be $\phi$, need to be accounted for, in addition to the 180° pulses of the PRS. Otherwise the analysis is very similar. Thus, the detected signal can be expressed as $M_t \sin \phi$.

$$M_t(t_{n+1}) = (M_t(t_n) + \Delta M_t(t_n))(-1)^{S_n} \cos\phi \quad [5]$$

$$\Delta M_t(t_n) = \frac{M_t^0 - M_t(t_n)}{T_{t1}} TR + CBF\left\{M_a(t_n) - \frac{M_t(t_n)}{\lambda}\right\}$$

$$M_t(t_{n+1}) = [M_t^0 \delta_t + M_t(t_n)(1-\varepsilon_t) + CBF \cdot M_a(t_n)TR](-1)^{S_n}\cos\phi$$

$$\text{where } \delta_t = \frac{TR}{T_{t1}} \text{ and } \varepsilon_t = \left(\frac{1}{T_{t1}} + \frac{CBF}{\lambda}\right)TR$$

$$= [M_t^0\delta_t + [M_t^0\delta_t + M_t(t_{n-1})(1-\varepsilon_t) + CBF \cdot M_a(t_{n-1})TR] \quad [5]$$
$$(-1)^{S_{n-1}}\cos\phi(1-\varepsilon_t) + CBF \cdot M_a(t_n)TR](-1)^{S_n}\cos\phi$$

$$= \left[M_t^0\delta_t + \begin{bmatrix} M_t^0\delta_t + [M_t^0\delta_t + M_t(t_{n-2})(1-\varepsilon_t) + CBF \cdot M_a(t_{n-2})TR] \\ (-1)^{S_{n-2}}\cos\phi(1-\varepsilon_t) + CBF \cdot M_a(t_{n-1})TR \\ (-1)^{S_{n-1}}\cos\phi(1-\varepsilon_t) + CBF \cdot M_a(t_n)TR \end{bmatrix}\right]$$

$$(-1)^{S_n}\cos\phi = M_t^0\delta_t(-1)^{S_n}\cos$$
$$\phi[1 + (-1)^{S_{n-1}}(1-\varepsilon_t)\cos\phi\{1 + (-1)^{S_{n-2}}(1-\varepsilon_t)\cos\phi\}] +$$
$$CBF \cdot M_t(t_{n-2})(1-\varepsilon_t)^3\cos^3\phi(-1)^{S_{n-2}+S_{n-1}+S_n} +$$
$$CBF \cdot TR(M_a(t_n)(-1)^{S_n}\cos\phi + M_a(t_{n-1})(-1)^{S_n+S_{n-1}}(1-\varepsilon_t)\cos^2\phi +$$
$$M_a(t_{n-2})(-1)^{S_n+S_{n-1}+S_{n-2}}(1-\varepsilon_t)^2\cos^3\phi)$$

after a total of N substitutions we have $$= M_t^0\delta_t\cos\phi\sum_{i=0}^{N}(1-\varepsilon_t)^i\cos^i\phi(-1)^{\sum_{j=0}^{i}S_{n-j}} +$$

$$M_t(t_{n-N})(1-\varepsilon_t)^{N+1}\cos^{N+1}\phi(-1)^{\sum_{j=0}^{N}S_{n-j}} +$$

$$CBF \cdot TR \cdot \cos\phi\sum_{i=0}^{N}M_a(t_{n-i})(-1)^{\sum_{j=0}^{i}S_{n-j}}(1-\varepsilon_t)^i\cos^i\phi$$

and the limit needs to be taken as N goes to infinity, or at least such that NTR>>$T_{t1}$ or $T_{a1}$, so as to reach a steady state. In such case the middle term goes to zero because of $(1-\varepsilon_t)^{N+1}$. This then gives an equation for the magnetization in the tissue:

$$M_t(t_n) = M_t^0\delta_t\cos\phi\sum_{i=0}^{N}(1-\varepsilon_t)^i\cos^i\phi(-1)^{\sum_{j=0}^{i}S_{n-j-1}} +$$

$$CBF \cdot TR \cdot \cos\phi\sum_{i=0}^{N}M_a(t_{n-i-1})(1-\varepsilon_t)^i\cos^i\phi(-1)^{\sum_{j=0}^{i}S_{n-j-1}}$$

$$= \cos\phi\sum_{i=0}^{N}\{CBF \cdot TR \cdot M_a(t_{n-i-1}) + M_t^0\delta_t\}$$

$$(1-\varepsilon_t)^i\cos^i\phi(-1)^{\sum_{j=0}^{i}S_{n-j-1}}$$

Remembering that the detected signals is the magnetization before the $\phi$ pulse times sin $\phi$ we find using equation [3]

$$M_a(t_n) = M^0\sum_{k=0}^{N_f}P_{n,k}(1-\delta_a)^{k-1}f(t_k) = \quad [6]$$

$$M^0Pg \text{ where } P_{n,k} = (-1)^{\sum_{j=0}^{k}S_{n-j-1}} +$$

$$\delta_a\sum_{i=0}^{k}(1-\delta_a)^{i-k-1}(-1)^{\sum_{j=0}^{i}S_{n-j-1}} \text{ and } g_k =$$

$$(1-\delta_a)^{k+1}f(t_k)$$

$$S_t(t_n) = \sin\phi\sum_{i=0}^{N}\left\{CBF \cdot TR \cdot M_a^0\sum_{k=0}^{N_f}P_{n-i-1k}(1-\delta_a)^{k+1}\right.$$

$$f(t_k) + M_t^0\delta_t\}(1-\varepsilon_t)^i\cos^i\phi(-1)^{\sum_{j=0}^{i}S_{n-j-1}}$$

$$= \sin\phi M^0\sum_{i=0}^{N}\left\{CBF \cdot TR \cdot \sum_{k=0}^{N_f}P_{n-i-1k}(1-\delta_a)^{k+1}f(t_k) + \delta_t\right\}$$

$$(1-\varepsilon_t)^i\cos^i\phi(-1)^{\sum_{j=0}^{i}S_{n-j-1}}$$

$$M_a(t_n) = M^0\sum_{k=0}^{N_f}P_{n,k}(1-\delta_a)^{k+1}f(t_k) = M^0Pg \text{ where } P_{n,k} =$$

$$(-1)^{\sum_{j=0}^{k}S_{n-j-1}} + \delta_a\sum_{i=0}^{k}(1-\delta_a)^{i-k-1}(-1)^{\sum_{j=0}^{i}S_{n-j-1}} \text{ and } g_k =$$

$$(1-\delta_a)^{k+1}f(t_k)$$

-continued $$S_t(t_n) = \sin\phi \sum_{i=0}^{N} \left\{ CBF \cdot TR \cdot M_a^0 \sum_{k=0}^{N_f} P_{n-i-1k}(1-\delta_a)^{k+1} f(t_k) + M_t^0 \delta_t \right\}$$

$$(1-\varepsilon_t)^i \cos^i \varphi (-1)^{\sum_{j=0}^{i} S_{n-j-1}}$$

$$= \sin\phi M^0 \sum_{i=0}^{N} \left\{ CBF \cdot TR \cdot \sum_{k=0}^{N_f} P_{n-i-1k}(1-\delta_a)^{k+1} f(t_k) + \delta_t \right\}$$

$$(1-\varepsilon_t)^i \cos^i \phi (-1)^{\sum_{j=0}^{i} S_{n-j-1}}.$$

The solution has two parts. The first term in the brackets is due to the spins exchanging into the tissue from the arterial blood. The second term in the brackets is due to the static spins in the tissue. Because of the linearity of the system this can be analyzed by assuming that $f(t_k)=\delta_{mk}$, i.e., the only transit time is mTR. This gives $$S_t(t_n) = \sin\phi M^0 \sum_{i=0}^{N} \{CBF \cdot TR \cdot (1-\delta_a)^{m+1} P_{n-i-1m} + \delta_t\}$$

$$(1-\varepsilon_t)^i \cos^i \phi (-1)^{\sum_{j=0}^{i} S_{n-j-1}}$$

$$= \sin\phi M^0 \sum_{i=0}^{N} \left\{ CBF \cdot TR \left( (-1)^{\sum_{j=0}^{m} S_{n-i-j-2}} + \delta_a \sum_{l=0}^{m} \right. \right.$$

$$\left. \left. (1-\delta_a)^{l-m-1}(-1)^{\sum_{j=0}^{i} S_{n-i-j-2}} \right) (1-\delta_a)^{m+1} + \delta_t \right\}$$

$$(1-\varepsilon_t)^i \cos^i \phi (-1)^{\sum_{j=0}^{i} S_{n-j-1}}$$

Ignoring the second term in the inner brackets, because it is small relative to the first, the following can be obtained:

$$S_t(t_n) = \sin\phi M^0 \sum_{i=0}^{N} \left\{ CBF \cdot TR \cdot (-1)^{\sum_{j=0}^{m} S_{n-i-j-2}}(1-\delta_a)^{m+1} + \delta_t \right\} \quad [7]$$

$$(1-\varepsilon_t)^i \cos^i \phi (-1)^{\sum_{j=0}^{i} S_{n-j-1}}$$

$$= \sin\phi M^0 \sum_{i=0}^{N} \left\{ \delta_t (1-\varepsilon_t)^i \cos^i \phi (-1)^{\sum_{j=0}^{i} S_{n-j-1}} + \right.$$

$$CBF \cdot TR \cdot (1-\delta_a)^{m+1}(1-\varepsilon_t)^i \cos^i \phi (-1)^{\sum_{j=0}^{m} S_{n-i-j-2}}$$

$$\left. (-1)^{\sum_{j=0}^{i} S_{n-j-1}} \right\}$$

$$\sin\phi M^0 \sum_{i=0}^{N} \{\delta_t P_{n,i} G_i + CBF \cdot TR \cdot (1-\delta_a)^{m+1} P_{n,i+m+1} G_i\}$$

where $G_i = (1-\varepsilon_t)^i \cos^i \phi$ and $P_{n,i} = (-1)^{\sum_{j=0}^{i} S_{n-j-1}}$ The static spins will appear in the transformed images at zero transit time and decay as $(1-\epsilon_t)^i \cos^i \phi$. The arterial spins that arrived at the tissue after a transit time of (m+1)TR, which have decayed only as $(1-\Delta_a)^{m+1}$ and which were exchanged into the tissue will then also decay as $(1-\epsilon_t)^i \cos^i \phi$. Thus, two components are expected to be seen in the transit time images: (i) an initial component that decays to zero followed by (ii) a rising peak that represents the CBF that subsequently decays. In exemplary embodiments of the disclosed subject matter, by varying the excitation angle these decay rates can be controlled and the two parts of the curve can be independently identified.

Determination of CBF

An important case occurs when $\phi=\pi/2$. Then only the arrival of the arterial spins are seen since $\cos\phi=0$ and thus the only term in the sum over i is i=0. This provides an assumption free method of determining CBF because the transit time distribution can be determined as next described.

Going back to equation [6], the following can be obtained:

$$S_t(t_n) = M^0 \left\{ CBF \cdot TR \cdot \sum_{k=0}^{N_f} P_{n-1k}(1-\delta_a)^{k+1} f(t_k) + \delta_t \right\} \text{ Let}$$

$$\Delta I(\vec{r}, t_l) = \sum_{j=0}^{N-1} P_{ij}^{-1} S_t(t_{j+1})$$

$$= \sum_{j=0}^{N-1} P_{ij}^{-1} M^0 \left\{ CBF \cdot TR \cdot \sum_{k=0}^{N_f} P_{jk}(1-\delta_a)^{k+1} f(t_k) + \delta_t \right\}$$

$$= M^0 \left\{ CBF \cdot TR \cdot \sum_{j=0}^{N-1} P_{ij}^{-1} \sum_{k=0}^{N_f} P_{jk}(1-\delta_a)^{k+1} f(t_k) + \right.$$

$$\left. \sum_{j=0}^{N-1} P_{ij}^{-1} \delta_t \right\}$$

$$\Delta I(\vec{r}, t_l) = M^0 \left\{ CBF \cdot TR \cdot (1-\delta_a)^{l+1} f(t_l) + \sum_{j=0}^{N-1} P_{ij}^{-1} \delta_t \right\}$$

$$= M^0 \cdot CBF \cdot TR \cdot (1-\delta_a)^{l+1} f(t_l) + M^0 \cdot \delta_t \cdot R_l$$

where $R_l = \sum_{j=0}^{N-1} P_{ij}^{-1}$ $M^0 \cdot \delta$ can then be estimated form both long and short transit times when $f(t_l)$ is zero as $R_I$ is known. Let it be Q, for example. Then an expression for CBF can be calculated at each point r using the fact that the integral of f is 1.

$$M^0 \cdot CBF(\vec{r}) \cdot TR \cdot f(t_l) = \frac{\Delta I(r, t_l) - QR_l}{(1-\delta_a)^{l+1}}. \text{ Since } \sum_{l=0}^{N_f} f(t_l) = 1$$

$$M^0 \cdot CBF(\vec{r}) \cdot TR = \sum_{l=0}^{N_f} \frac{\Delta I(\vec{r}, t_l) - QR_l}{(1-\delta_a)^{l+1}}$$

Since we know $M^0=Q/\delta_t$ we obtain the following formula for CBF:

$$CBF(\vec{r}) = \frac{\delta_t}{Q \cdot TR} \sum_{l=0}^{N_f} \frac{\Delta I(\vec{r}, t_l) - QR_l}{(1-\delta_a)^{l+1}} = \frac{1}{Q \cdot T_{t1}} \sum_{l=0}^{N_f} \frac{\Delta I(\vec{r}, t_l) - QR_l}{(1-\delta_a)^{l+1}}$$

in ml/sec/gr

This expression demonstrates the value of PRAM in ASL measurements inasmuch as it shows the independence of the method to variations in transit time distribution. Of course, if the transit time is very slow, say 3 or 4 $T_{a1}$'s, then the division by $(1-\Delta_a)^{l+1}$ becomes untenable. Even for normal transit times this problem requires cutting off the sum at the point determined when the SNR is one, that is when the individual terms have reached the noise level in the particular experiment in exemplary embodiments of the disclosed subject matter.

Using exemplary systems and methods according to the disclosed subject matter, the following experiments were performed.

Figure 4:
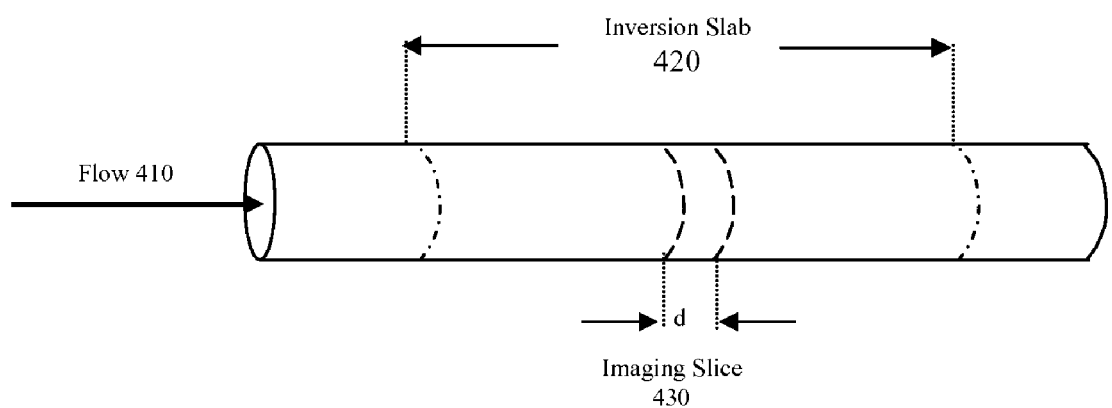
FIG. 4 illustrates the relationship between a PRAM inversion slab and an imaging slice according to an exemplary embodiment of the disclosed subject matter.

In one experiment, images were acquired on an 89 mm vertical bore 9.4 T Bruker Biospin imager. A gradient echo sequence was used with a variable selective 180° pulse inserted immediately before the imaging block. The 180° pulse, which inverted a 20 mm wide region, was either on or off depending on the value of the element in a 63 element long PRS which was chosen to provide more than 3 seconds of length for a TR of 50 msec so that slow velocities would be observable. The imaged slice was in the middle of this region and was 1 mm thick. The relationship of the inversion slab and the imaged slice is depicted in FIG. 4 with d=1 cm, where flow 410 is depicted as running through inversion slab 420 from left to right in the figure. Imaging slice 430 was in the middle of the inversion slab, as noted. Imaging parameters were FOV 20 mm, TR 50, 100 and 200 ms, matrix 64×64, and flip angle=45°. A total of 63×64 transients were acquired, cycling through the PRS once for each k-space line. The flow phantom consisted of a 1.27 cm inner diameter (i.d.) Tygon tube containing water running through the RF coil of 3 cm i.d. A computer-controlled pump (Masterflex L/S) circulated the water in a closed loop. Flows were varied from 50 to 200 mL/min.

Figure 5:
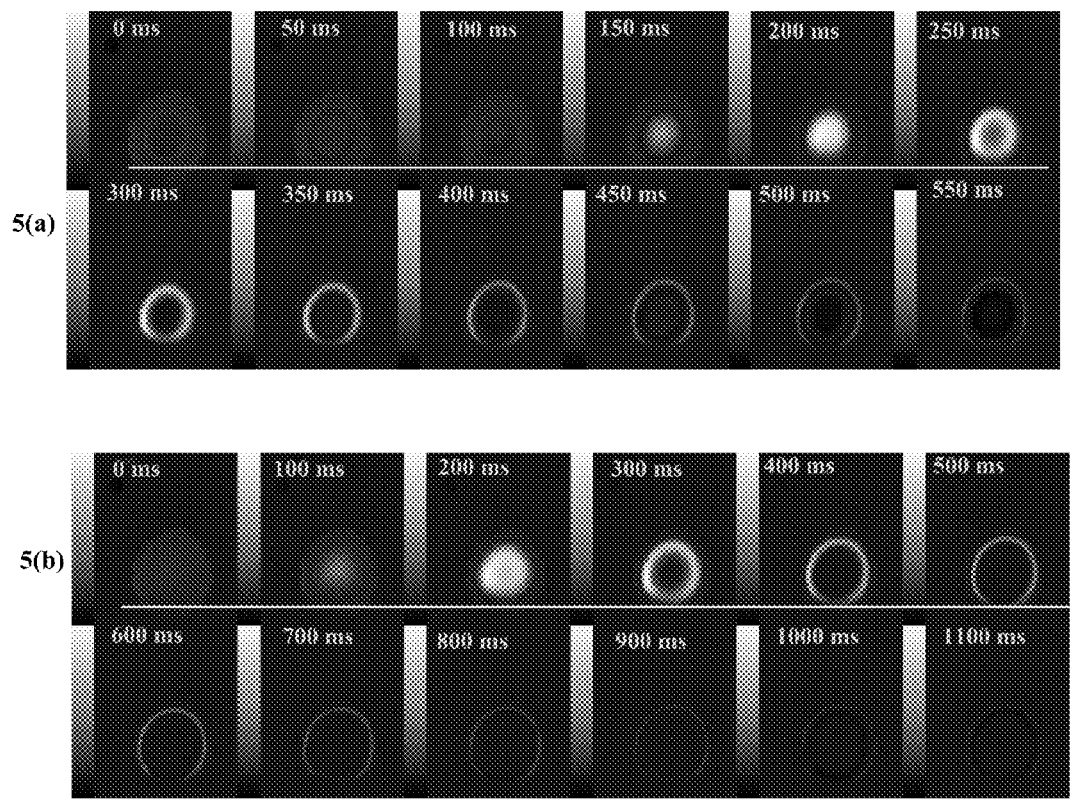
FIGS. 5(a)-(b) are images showing exemplary reconstructed transit time distributions at 200 mL/min according to an exemplary embodiment of the disclosed subject matter.
Figure 6:
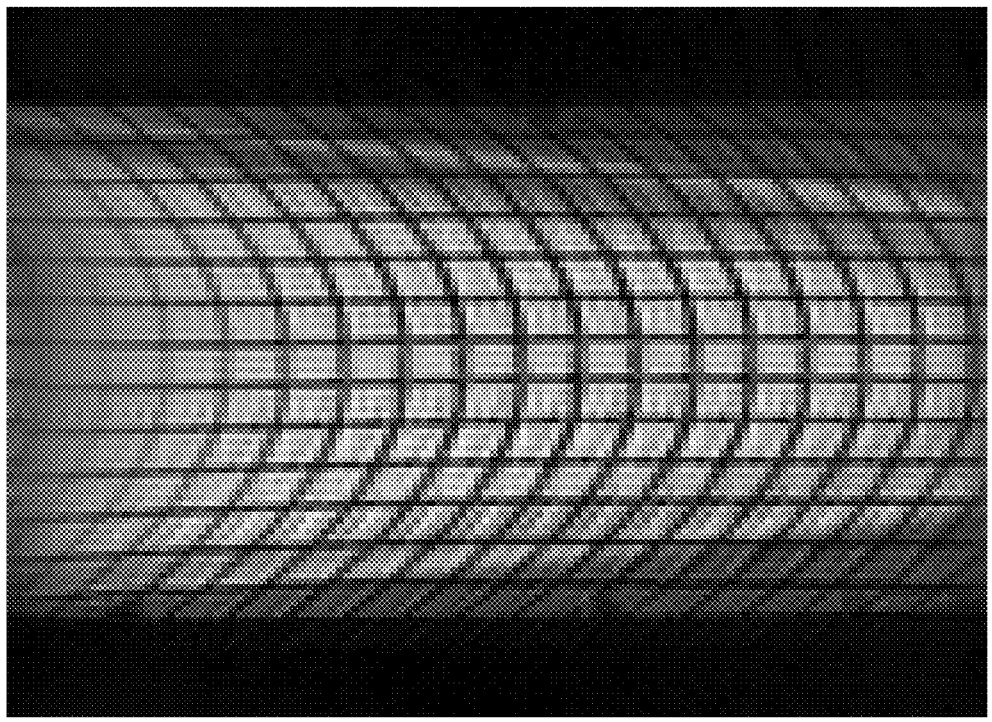
FIG. 6 depicts the results of a tagging experiment on a flow phantom according to an exemplary embodiment of the disclosed subject matter.

At the flow rates used, flow was found to be non turbulent with a parabolic velocity distribution across the tube. The sequential transit time images of the flow distribution f after the inversion shown in equation [1] are displayed in FIG. 5 for TR=50 ms (FIG. 5($a$)), and TR=100 ms (FIG. 5($b$)), for a bulk flow of 200 mL/min, respectively. The results of a tagging experiment are shown in FIG. 6 (tags of 1.5 mm spacing, imaged after 200 ms) which demonstrates a parabolic distribution. Inspection of FIG. 5 reveals that each later transit image shows a wider and wider ring corresponding to a longer transit time. Comparison of the two different TRs shows similar patterns at the same transit time delay. This can be seen, for example, by comparing the second image from the left in the bottom row of FIG. 5($a$) ($8^{th}$ image or 400 ms) with the fourth image from the left in the top row of FIG. 5($b$) ($4^{th}$ image or 400 ms). From the equations of Poisseuille flow the theoretical maximum velocity in the center of the phantom can be calculated to be 5.26 cm/s, corresponding to a transit time of 190 ms.

Figure 7:
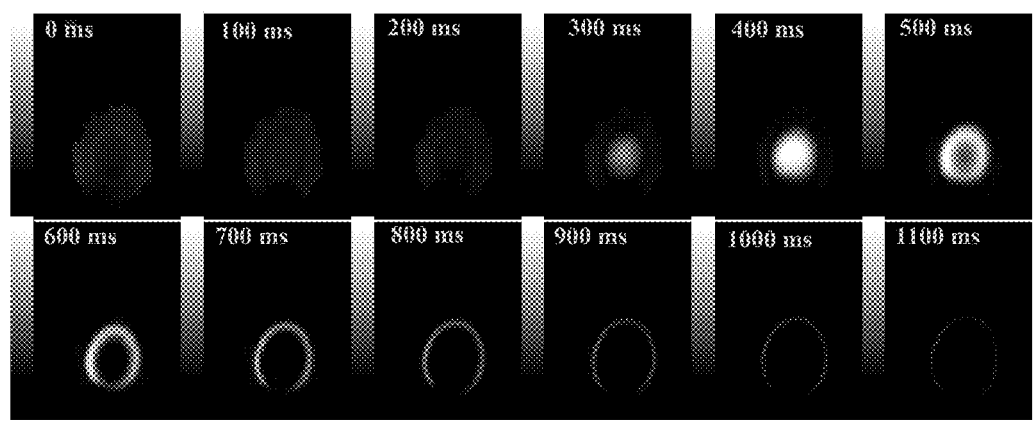
FIG. 7 depicts images showing reconstructed transit time distributions at 100 mL/min according to an exemplary embodiment of the disclosed subject matter.

In this experiment, several different flow rates and TR were also investigated. FIG. 7, for example, shows reconstructed transit time images of f for TR=100 ms for a flow of 100 mL/min, as compared with those of FIG. 5$a$ obtained for 200 mL/min at TR=50 ms. In all cases the observed transit time pattern was consistent with the theoretical velocities. As can be seen, the signal at the center of the tube in the transit time images appears at the time predicted by the theory. Furthermore, the images clearly reflect the expected parabolic shape.

Figure 8:
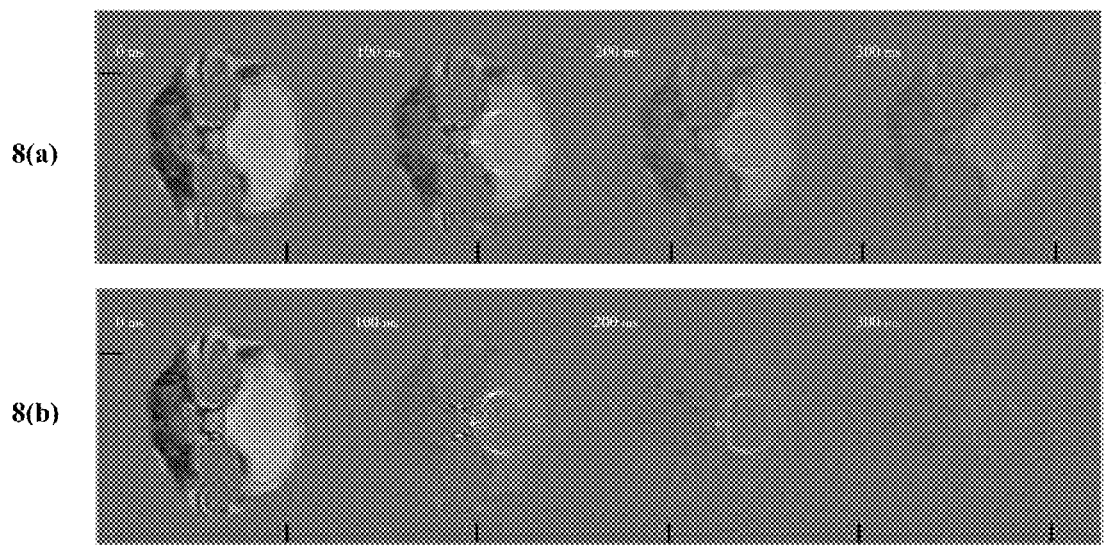
FIGS. 8(a)-(b) depict PRAM images of a mouse brain according to an exemplary embodiment of the disclosed subject matter.

In addition to the flow phantom studies described above, experiments were conducted on normal anaesthetized mice with a 1.6 cm inversion slab positioned so that the inversion plane for the inflowing blood was 8 mm away from the imaged slice. Data was acquired at TR=100 ms with both 45° and 90° excitation angles with a matrix of 128×128 and a FOV of 2.5 cm and 1 mm slice thickness. As in the flow phantom, the PRS was cycled at each phase encode step. Acquisition time was approximately 15 minutes. A typical result is shown in FIG. 8 which compares the reconstructed images at the two angles for transit times of 0, 100, 200 and 300 ms, respectively. FIG. 8($a$) depicts images acquired with Flip Angle=45°, and FIG. 8($b$) depicts images acquired with Flip Angle=90°. As can be seen with reference to FIG. 8, in both cases the first image has considerable structure from the mouse brain and head. However, this structure almost completely disappears by 100 ms for the 90° pulse case while it is still visible at 300 ms for the 45° case. This result is completely consistent with the theoretical predictions of equation [7] above, namely that the static spins will be visible only in the first reconstructed image for 90° but will decay as $(1-\epsilon_t)^i \cos^i \phi$ for f not equal to $\pi/2$. Also of note is the close agreement between the arterial brightening seen in the two cases. As discussed in connection with equation [3] above, the arterial flow is expected to be relatively independent of the pulse angle because it only experiences the excitation pulse once (assuming that all flow is proximal to the imaged slice). These data show that with the flexibility that PRAM provides it can be possible to cleanly separate static spins from flowing spins by varying the excitation angle.

Thus, in exemplary embodiments of the disclosed subject matter, Pseudo Random Amplitude Modulation (PRAM) can be used to acquire transit time data in ASL in a completely novel way. This enables PRAM to obtain CBF values without the problem of transit time effects. As described in the theoretical analysis above, in exemplary embodiments of the disclosed subject matter it is possible to directly estimate the local CBF with no assumptions beyond the arterial and tissue relaxation times. PRAM (as well as other modulation functions or sequences satisfying the criteria of "complexity" provided above) is able to do this because it can directly measure the local transit time distribution arterial distribution, essentially normalizing the arterial input function. Further, exemplary methods have a duty cycle of approximately 50% and do not require separate control and labeled images, as the entire sequence is used to calculate the complete time course of the spins moving from the labeling plane to the imaging plane. Similar results can be achieved using other complex modulation schemes.

Thus, in exemplary embodiments of the disclosed subject matter, an assumption free method of estimating the CBF at each point in the image can be implemented, removing the uncertainty regarding time distributions that has hitherto made absolute quantitation difficult in ASL.

In exemplary embodiments of the disclosed subject matter, a scanner can be programmed to generate a desired complex modulation function, such as, for example, a PRS, in conjunction with imaging sequences. Such programs can be, for example, written in a scanner optimized language such as, for example, the Phillips programming code GOAL C for implementation on a Phillips scanner, or using other known programming languages as may be desired.

Figure 11:
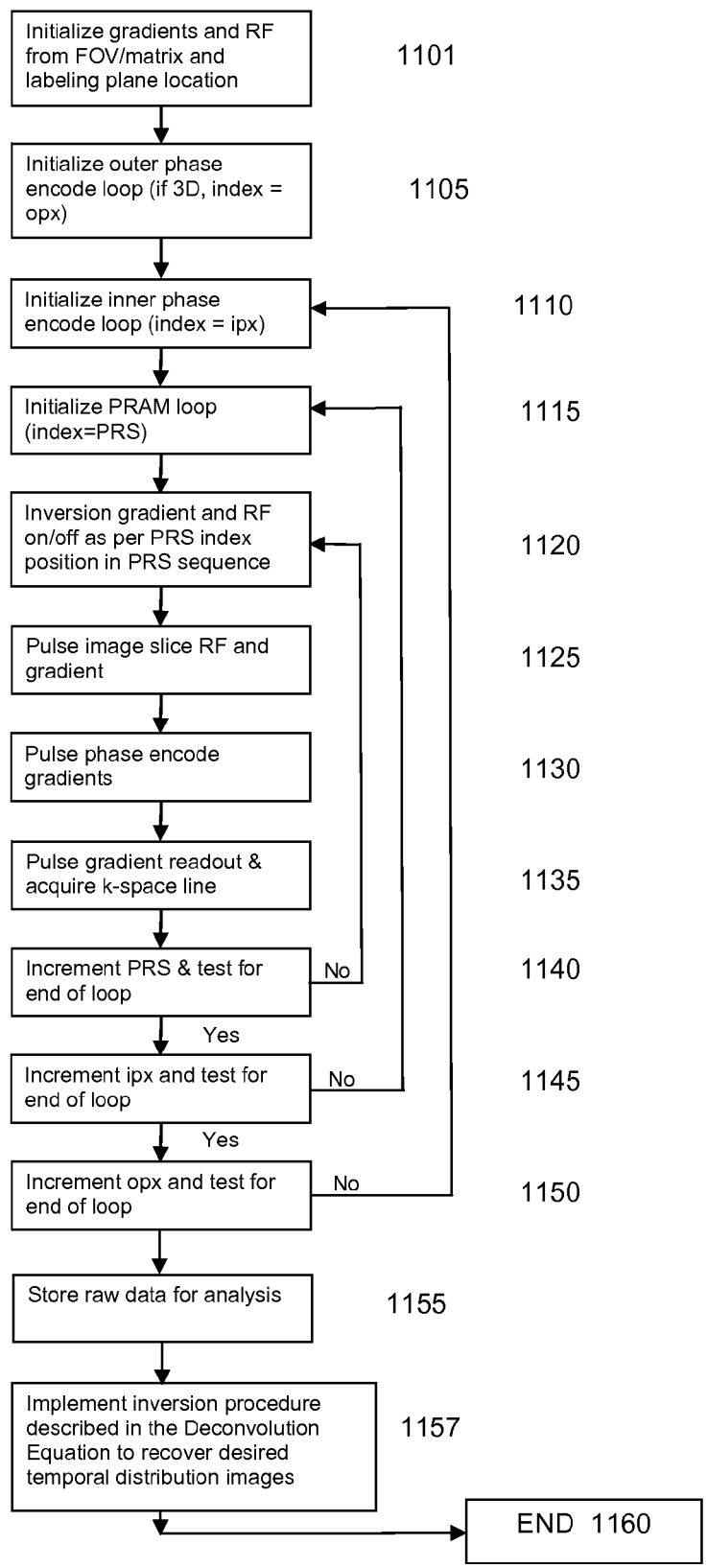
FIG. 11 depicts an exemplary process flow according to an exemplary embodiment of the disclosed subject matter.

In exemplary embodiments of the disclosed subject matter, an exemplary process flow such as that depicted in FIG. 11 can be implemented with a series of instructions to be executed by a computer or other data processor. Such computer or other data processor can be, for example, integrated within an MRI machine and such series of instructions can be used to control such an MRI machine to implement methods according to an exemplary embodiment of the disclosed subject matter.

With reference to FIG. 11, such process flow will next be described using an exemplary PRS as a modulation function. At 1101, gradients and RF can be initialized from a field of view matrix and a labeling plane location. From there process flow can, for example, move to 1105 where an outer phase encode loop can be initialized (using an index "opx") if it is desired to image a 3D block of tissue rather than a single slice. Continuing at 1110, an inner phase encode loop can be initialized, using, for example, an index "ipx". Process flow can then continue, for example, to 1115 where a PRAM loop can be initialized, using, for example, an index "PRS."

At 1120, inversion gradient and RF on/off can be implemented according to the PRS index position in the PRS sequence. At 1125, image slice RF and gradient can be pulsed, at 1130, the phase encode gradients can be pulsed, and at 1135, for example, the gradient readout can be pulsed and a k-space line can be acquired. At 1140, for example, the PRS can be incremented and the system can then test for an end of loop. If an end of loop has been reached, process flow can move to 1145. If not, process flow can return, for example, to 1120. If process flow moves to 1145 at 1140, then the ipx index (the inner phase encode loop index) can be incremented and the system can once again test for an end of loop. If it has reached an end of loop, then process flow can, for example, move to 1150. If no end of loop has been reached at 1145, then, for example, process flow can return to 1115. If process flow at 1145 has moved to 1150, then an outer phase index (here "opx") can be incremented, and the system can test for an end of loop. If at 1150 an end of loop has not been reached then process flow can, for example, return to 1110, and the process flow shown at 1110 through 1150 can repeat. If at 1150 an end of loop in the outer phase encoding loop has been detected, then process flow can move to 1155 where raw data obtained via the processing described above can be stored for analysis, and process flow can move to 1157 where an inversion procedure can be implemented as, for example, described in the Deconvolution Equation presented above, to recover desired temporal distribution images. From 1157 process flow can, for example, move to 1160 where it then ends.

Additionally, a more general loop structure can be implemented that can be used with receive-only coils and standard gradient and imaging sequences in addition to EPI.

Figure 9:
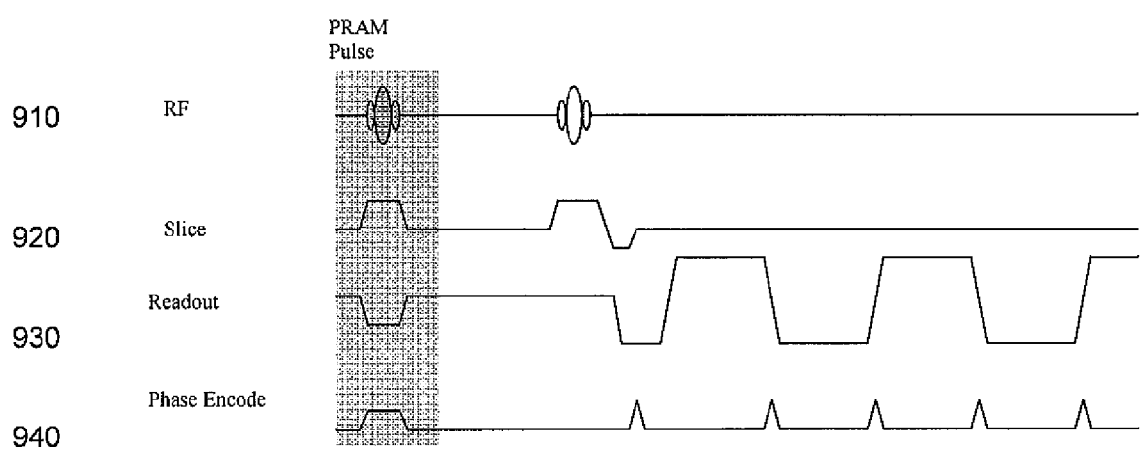
FIG. 9 is a schematic representation of a PRAM 180° pulse location according to an exemplary embodiment of the disclosed subject matter.

In an exemplary implementation according to the disclosed subject matter, a PRS can be relatively easily implemented by modifying a standard EPI sequence used to acquire TILT images[12], since such a sequence already contains the needed 0°/180° RF and gradient pulses in a loop around the EPI acquisition code. Because the existing sequence only allows use of a transmit-receive ("T/R") coil, this can be done, for example, using a standard Phillips T/R head coil. The necessary additions to such a standard imaging sequence are highlighted schematically in FIG. 9. FIG. 9 depicts four rows, being RF 910, slice 920, readout 930, and phase encode 940. Such additions can consist of, for example, inserting a selective RF pulse and gradient waveform at the beginning of the sequence, which are contemplated and which are in a control loop that can modulate an RF pulse for either a 0° or 180° flip according to a given PRS sequence, as described above.

Schematically, an exemplary location of a new PRS controlled RF pulse and gradient waveform is illustrated in FIG. 9. As is illustrated in this figure, the slice selection gradient does not have to be parallel in the PRAM inversion pulse and the imaged slice.

To implement the example implementation, code modifications can, for example, involve altering the loop control structure for the existing TILT pulses so that it can handle 63 PRAM pulses. N=63 was chosen because of successful results found at 9.4 T with this sequence. In addition, the correct dynamic scanning loops must be enabled since a single pass through the PRS cycle will not have sufficient SNR. It is estimated that approximately 5 to 10 minutes of acquisition will be needed to achieve adequate SNR. After acquisition, raw data can be transferred to, for example, a computer for analysis. Analysis can consist of, for example, Fourier transforming the k-space data to produce individual images measured at each point in the PRS cycle. These images can then, for example, be deconvolved as described above.

Figure 10:
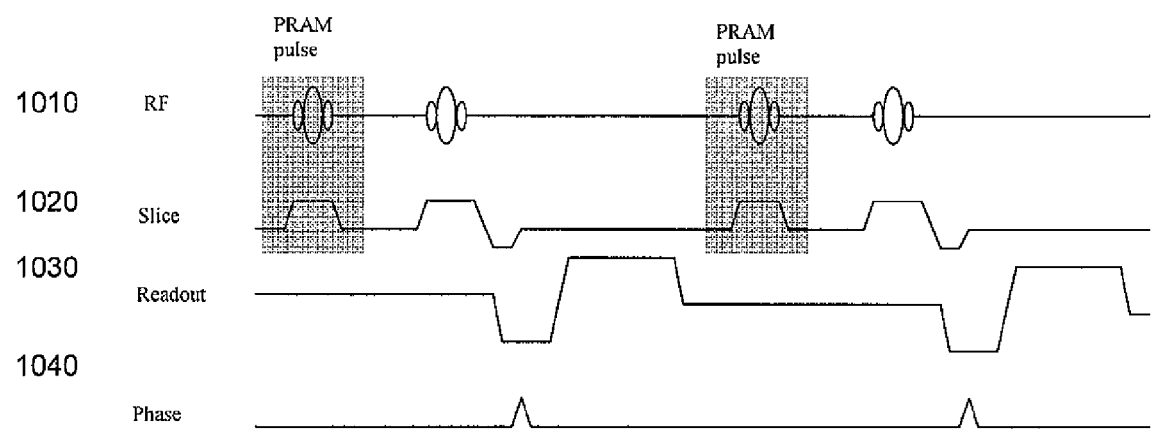
FIG. 10 is a schematic representation of a PRAM 180° pulse location inside a phase encode loop according to an exemplary embodiment of the disclosed subject matter.

In another exemplary implementation of the disclosed subject matter, a code module that can be inserted in a standard gradient echo imaging sequence can, for example, be developed. This can, for example, incorporate a PRS (or similar complex modulation sequence) loop inside the phase encode loop as is illustrated in FIG. 10. FIG. 10 depicts the same rows as are shown in FIG. 9, being RF 1010, slice 1020, readout 1030, and phase encode 1040. Such a code module can include, for example, insertion of the PRS loop and generation of appropriate validation code required for the scanner to operate within the safety limits set by the FDA. This can be done, for example, by adaptation of a cardiac phase cycle loop which already exists inside the phase encode loop. This can, for example, enable the PRS to repeat once for each value of the phase encode gradient needed to generate the desired image. As before, the dynamic loop structures must be enabled to allow multiple acquisitions. Once such a module has been developed for gradient echo sequences it can, for example, be extended to spin echo sequences by inserting appropriate 180° pulses during the readout. The extra pulses can be accounted for in the theory by balancing the readout gradients and the use of 180°-φ pulses to excite the imaged slice so that the net effect is still only that of a φ pulse since a 360° pulse does not excite the spins in any way. Raw data can be saved directly as it is acquired and later transferred to, for example, a computer for analysis.

In exemplary embodiments of the disclosed subject matter a prospective PRAM sequence can be thoroughly tested and validated using a flow phantom consisting of both stationary and flowing spins. To do this, for example, a cylindrical sample (i.d. 10 cm) with a continuous tube (i.d. 2 cm) through its center can be constructed. The tube can be connected to a variable speed pump so that the flow can be adjusted. The maximum speed in the center of the tube can range, for example, from 1 to 20 cm/sec.

As noted above, a PRAM procedure depends on the TR, the PRS length (n), the distance from the edge of the inversion slab to the imaged plane, the excitation pulse angle, the slice thickness, and the flow rate. The relationship among the TR, distance between the inversion plane and the imaged slice, and the flow speed is simply v=d/t.

Thus, PRAM images can be acquired at five different flows, corresponding to maximum velocities of 1, 2, 5, 10 and 20 cm/s. The FOV can be, for example, 128 by 128 mm acquired with a 64×64 matrix, leading to 2 mm in-plane resolution. This can provide sufficient resolution over the tube to resolve the expected parabolic velocity profile, i.e. highest intensity at the center of the image. An initial PRS, $\{A_n\}$, used can be 63 elements long, generated by a linear shift register using, for example, the polynomial, $x^6+x+1$, and can be, for example:

$\{A_n\}$={-1,1,-1,1,-1,1,-1,-1,1,1,-1,-1,1,1,-1,-1,1,1,-
1,-1,1,-1,1,1,-1,1,1,1,-1,-1,-1,1,1,1,1,-1,1,-1,-1,-
1,-1,1,1,1,-1,1,-1,1,1,1,1,-1,-1,1,1,1,1,1,-1,1,1,1,1,1,
1,-1,-1,-1,-1,1}.

Each image acquired can, for example, be stored as raw k-space data and subsequently transferred to a computer or data processor, such as for example, a PowerEdge™ 6800, for further processing using, for example, Matlab programs written to carry out the matrix inversions described above. If a longer PRS is needed then a prime polynomial of seventh degree ($x^7+x+1$) can be used, for example, to generate a 127 element sequence. A longer sequence may, for example, be needed to study very short TR's since the product of PRS length and TR needs to be longer than the difference in transit time between the fastest and slowest velocities in order to prevent overlap between the slowest velocities from the previous PRS cycle and the fastest velocities from the present cycle.

At each flow rate (for example, 1, 2, 5, 10, 20 cm/s) the TR can be varied, such as, for example, as 50, 100, 150, 200 and 250 ms. Additionally, for example, the distance from the edge of the inversion slab to the imaged slice (2, 5 and 10 cm), and the slice excitation angle (20°, 45° and 90°) and imaged slice thickness (2 and 10 mm) can be varied. To keep the number of separate acquisitions reasonable, the parameters can typically be varied over the indicated range at, for example, one or two sets of values of the remaining parameters.

In addition to PRAM acquisitions at each flow rate, standard spin tagging can also be used to directly measure the actual velocities in the tube. Furthermore, CASL images with five post labeling delays and the inversion plane set at the edge of the PRAM inversion slab can be acquired. The shortest PLD can, for example, be chosen to allow the labeled spins to clear at the maximum velocity (so that the center of tube will just be unlabeled). Four additional acquisitions can, for example, each have their PLD increased by a factor of $3^{1/4}$ in order to acquire of a range of images with the labeled spins cleared from increasing larger radii. With this choice of multiplicative factor the longest PLD should correspond to a velocity found at a diameter of 1.8 cm assuming a parabolic velocity distribution. These images can, for example, then be compared to the sum of the transformed PRAM results from the PLD onward in transit times. Images from the CASL sequences and the summed transformed PRAM images can be compared by examining profiles to determine the radii where the labeled spins vanish at each post labeling delay.

Using exemplary systems and methods according to the disclosed subject matter, the following described experiments could, for example, be run.

A first exemplary experiment could be run to confirm that a PRAM sequence is producing expected data. Early transit time images produced by PRAM sequences can be tested for congruence with an arterial tree observed by the very well validated TOF MRA procedure. For example, six volunteers can participate in such an experiment. During two scanning sessions, a standard 3D T1 sequence at an isotropic resolution of 1.5 mm for anatomical reference can be acquired. Then 20 5 mm thick slices with a PRAM sequence verified as above be acquired. Since these acquisitions are designed to detect the signal from the arterial blood which is much higher than the signal from perfusion, they will need only a 1 minute acquisition for adequate S/N. Allowing 30 seconds for repositioning the slice, we expect that acquisition of the entire dataset will require a total of 30 minutes. Each slice can be moved superiorly so that a 10 cm thick block will ultimately be covered. The block can be positioned so the uppermost slice will be at the top of the brain. The raw data can be transformed and deconvolved to generated transit time images of each slice. The same region of the brain can then be imaged with standard TOF MRA and reconstructed using maximum intensity projection (MIP) algorithm on the scanner. The reconstructed MIP images can also be transferred to a computer. Both datasets can be examined using a 3D visualization program, for example, Almira, to confirm that the expected blood flow motion through the arterial tree observed by PRAM visually coregisters the detailed arterial anatomy seen on the MEP projections. Six volunteers can be used in order to sample a range of variations in normal anatomy.

In a second exemplary experiment, the results of CBF measurement could be, for example, obtained with PRAM and with CASL. Twelve volunteers can participate in such an experiment. Separate scans performed during two scanning sessions will cover different slice positions and will alternate between PRAM and CASL. PRAM data can be, for example, acquired with a 90° pulse to minimize the contributions from the static tissue and implement the CBF calculation procedure of equation [8]. These values can be compared to the CBF values obtained by CASL using the standard formulae of Alsop[14]. Further, the same slice can be acquired at several values of the excitation angle, as equation [7] shows that the trailing shape of the transit time curve in the tissue parenchyma is controlled by the decay rate $\epsilon$ but the uptake depends on the transit time distribution. In this way the static spin contributions can be clearly separated from the inflowing ones which contribute to the transit time distribution.

Because it is expected that the spread in transit times will be less than 3 seconds[14], the same 63 PRS can be used initially. Initial studies can, for example, be conducted with TR equal to 100 ms, although it will be possible to use a TR as small as 50 ms for a PRS cycle time of 3.15 seconds. High resolution, 3DT1 images (SPGR) can be acquired first for anatomical reference. The PRS cycle can be repeated 100 times in the PRAM sequence to increase SNR, resulting in a total acquisition time of 10.5 minutes. Three excitation pulse angles can be used, for example, 20°, 45°, and 90°. FOV and matrix can be 240×240 mm and 64×64 for a resolution of 3.75 mm. CASL sequences can be acquired with the same FOV and matrix and 5 different post labeling delays (400, 600, 800, 1000 and 1200 ms). Each acquisition can be 5 minutes, for a total of 20 minutes.

A voxel-wise comparison of the calculated flow for CASL for each PLD and PRAM according to the formula in equation [8] can, for example, then be obtained. It should be noted that for CASL, the CBF will vary with PLD reflecting the overall integral of the transit time larger than the PLD chosen.

The methods and systems of exemplary embodiments of the disclosed subject matter thus provide an inexpensive and non-invasive MRI technique for the diagnosis of diseases including dementia, stroke, ischemia, and brain tumors through the detection of pathological changes in cerebral blood flow that occur early in the pathogenesis of these conditions.

Moreover, such methods and systems can further contribute to the development of magnetic resonance imaging techniques that can be used for quantitative measurement of cerebral blood flow, which will benefit researchers and clinicians studying the brain.

While this invention has been described with reference to one or more exemplary embodiments thereof, it is not to be limited thereto and the appended claims are intended to be construed to encompass not only the specific forms and variants of the invention shown, but to further encompass such as may be devised by those skilled in the art without departing from the true scope of the invention. It is further understood that the various disclosed embodiments can be combined, rearranged, substituted, adapted, etc. as may be convenient or desirable, all such combinations, rearrangements, substitutions, adaptations, etc., being within the spirit and scope of the invention.

APPENDIX A

References

1. Ogawa, S., Lee, T. M., Kay, A R. & Tank, D. W. Brain magnetic resonance imaging with contrast dependent on blood oxygenation. *Proc Natl Acad Sci USA* 87, 9868-72 (1990).

2. Kety, S. S. & Schmidt, C. F. The determination of cerebral blood flow in man by use of nitrous oxide in low concentrations. *Am J Physiol.* 143, 53-66 (1945).
3. Ito, H., Kanno, I. & Fukuda, H. Human cerebral circulation: positron emission tomography studies. *Ann Nucl Med* 19, 65-74 (2005).
4. Williams, D. S., Detre, J. A. Leigh, J. S. & Koretsky, A. P. Magnetic resonance imaging of perfusion using spin inversion of arterial water. *Proc Natl Acad Sci USA* 89, 2 12-6 (1992).
5. Kwong, K. K., Wanke, I., Donahue, K. M., Davis, T. L. & Rosen, B. R. EPI imaging of global increase of brain MR signal with breath-hold preceded by breathing $O_2$. *Magn Reson Med* 33, 448-52 (1995).
6. Edelman, R. R. et al. Qualitative mapping of cerebral blood flow and functional localization with echo-planar MR imaging and signal targeting with alternating radio frequency. *Radiology* 192, 513-20 (1994).
7. Golay, X., Hendrikse, J. & Lim, T. C. Perfusion imaging using arterial spin labeling. *Top Magn Reson Imaging* 15, 10-27 (2004).
8. Barbier, E. L., Silva, A C., Kim, H. J., Williams, D. S. & Koretsky, A P. Perfusion analysis using dynamic arterial spin labeling (DASL). *Magn Reson Med* 41, 299-308 (1999).
9. Detre, J. A. et al. Tissue specific perfusion imaging using arterial spin labeling. *NMR Biomed* 7, 75-82 (1994).
10. Helpern, J. A., Branch, C. A., Yongbi, M. N. & Huang, N.C. Perfusion imaging by uninverted flow-sensitive alternating inversion recovery (UNFAIR). *Magn Reson Imaging* 15, 135-9 (1997).
11. Yongbi, M. N., Yang, Y., Frank, J. A. & Duyn, J. H. Multislice perfusion imaging in human brain using the C-FOCI inversion pulse: comparison with hyperbolic secant. *Magn Reson Med* 42, 1098-105 (1999).
12. Golay, X., Stuber, M., Pruessmann, K. P., Meier, D. & Boesiger, P. Transfer insensitive labeling technique (TILT): application to multislice functional perfusion imaging. *J Magn Reson Imaging* 9, 454-61 (1999).
13. Luh, W. M., Wong, E. C., Bandettini, P.A. & Hyde, J. S. QUIPSS II with thin-slice T11 periodic saturation: a method for improving accuracy of quantitative perfusion imaging using pulsed arterial spin labeling. *Magn Reson Med* 41, 1246-54 (1999).
14. Alsop, D. C. & Detre, J. A. Reduced transit-time sensitivity in noninvasive magnetic resonance imaging of human cerebral blood flow. *J Cereb Blood Flow Metab* 16, 1236-49 (1996).
15. Detre, J. A. & Wang, J. Technical aspects and utility of fMRI using BOLD and ASL. *Clin Neurophysiol* 113, 621-34 (2002).
16. Barbier E. L., Silva, A. C., Kim, S. G. & Koretsky, A. P. Perfusion imaging using dynamic arterial spin labeling (DASL). *Magn Reson Med* 45, 1021-9 (2001).
17. Knuth, D. E. *The Art of Computer Programming* (Addison-Wesley, Boston, 1998).
18. Buxton, R. B. Quantifying CBF with arterial spin labeling. *J Magn Reson Imaging* 22, 723-6 (2005)."

What is claimed:

1. A method for measuring a distribution of transit times of labeled spins in a sample via magnetic resonance imaging, comprising:
   providing a labeling plane and an imaging plane for a sample;
   modulating the magnetization of inflowing spins at the labeling plane using a complex sequence; and
   obtaining the distribution of transit times for the modulated spins from the labeling plane to each voxel of the imaging plane from a set of acquired image slices of the sample in a single unified acquisition,
   wherein the complex sequence has minimal autocorrelation over time and its frequency domain transform has no zeros, and wherein the frequency domain transform of the distribution of transit times is obtained by dividing the frequency domain transform of the acquired signal of each of the acquired image slices for each voxel by the frequency domain transform of the complex sequence on a voxel by voxel basis.

2. The method of claim 1, wherein the complex sequence is a pseudo random sequence having $2^n-1$ elements, where n is an integer greater than 1.

3. The method of claim 2, wherein the pseudo random sequence comprises one of 63 and 127 elements.

4. The method of claim 2, wherein the pseudo random sequence is cycled through once for each k-space line.

5. The method of claim 2, wherein the pseudo random sequence is used to modulate a 180° variable selective pulse applied to the sample.

6. The method of claim 1, wherein the complex sequence is used to modulate a 180° variable selective pulse applied to the sample.

7. The method of claim 2, wherein the sample is an artery, and wherein arterial longitudinal magnetization and flow distribution are related according to:

$$M_i = \sum_{j=0}^{N-1} M^0 (-1)^{\sum_{k=i}^{i-j} S_k} f_j,$$

wherein $M_i$ is the image observed at the $i^{th}$ element in the pseudo random sequence, $f_j$ is the spins that have taken j TR periods to move from the edge of an inversion slab to an imaging slice location, and $S_k$ is 0 or 1 depending on whether there had been a 180° pulse at a $k^{th}$ step of the pseudo random sequence.

8. The method of claim 7, wherein the complex sequence is a pseudo random sequence comprising $2^n-1$ elements, where n is an integer greater than 1.

9. The method of claim 2, wherein the number of image slices of the sample acquired equals the length of the pseudo-random sequence.

10. A system for measuring a distribution of transit times of labeled spins in a sample via magnetic resonance imaging, comprising:
   an MRI scanner;
   a data processor; and
   a controller,
   wherein in operation the controller executes a series of instructions which cause the MRI scanner to:
      provide a labeling plane and an imaging plane for a sample;
      modulate the magnetization of inflowing spins at the labeling plane using a complex sequence;
   and causes the data processor to:
      process an acquired signal at the imaging plane to obtain a distribution of transit times for the modulated spins from the labeling plane to each voxel of the imaging plane from a set of acquired image slices of the sample in a single unified acquisition,
   wherein the complex sequence has minimal autocorrelation over time and its frequency domain transform has no zeros, and wherein the frequency domain transform of the distribution of transit times is obtained by dividing the frequency domain transform of the acquired signal by the frequency domain transform of the complex sequence on a voxel by voxel basis.

11. The system of claim 10, wherein the complex sequence is a pseudo-random sequence having $2^n-1$ elements, where n is an integer greater than 1.

12. The system of claim 11, wherein the pseudo-random sequence comprises one of 63 and 127 elements.

13. The system of claim 11, wherein the pseudo-random sequence is cycled through once for each k-space line.

14. The system of claim 11, wherein the pseudo random sequence is used to modulate a 180° variable selective pulse applied to the sample.

15. The system of claim 10, wherein the complex sequence is used to modulate a 180° variable selective pulse applied to the sample.

16. The system of claim 15, wherein the complex sequence is a pseudo random sequence comprising $2^n-1$ elements, where n is an integer greater than 1.

17. The system of claim 11, wherein the sample is an artery, and wherein arterial longitudinal magnetization and flow distribution are related according to:

$$M_i = \sum_{j=0}^{N-1} M^0(-1)^{\sum_{k=i}^{i-j} S_k} f_j,$$

wherein $M_i$ is the image observed at the $i^{th}$ element in the pseudo random sequence, $f_j$ is the spins that have taken j TR periods to move from the edge of an inversion slab to an imaging slice location, and $S_k$ is 0 or 1 depending on whether there had been a 180° pulse at a $k^{th}$ step of the pseudo random sequence.

18. The system of claim 11, wherein the number of image slices of the sample acquired equals the length of the pseudo-random sequence.

19. The system of claim 10, wherein the number of image slices of the sample acquired equals the length of the complex sequence.

20. A computer program product comprising a tangible computer usable medium having computer readable program code embodied therein for causing a computer to:
provide a labeling plane and an imaging plane for a sample;
modulate the magnetization of inflowing spins at the labeling plane using a complex sequence; and
obtain a distribution of transit times for the modulated spins from the labeling plane to each voxel of the imaging plane from a set of acquired image slices of the sample in a single unified acquisition;
wherein the complex sequence has minimal autocorrelation over time and its frequency domain transform has no zeros, and
wherein the frequency domain transform of the distribution of transit times is obtained by dividing the frequency domain transform of the acquired signal of each of the acquired image slices by the frequency domain transform of the complex sequence on a voxel by voxel basis.

21. The computer program product of claim 20, wherein the complex sequence is a pseudo-random sequence having $2^n-1$ elements, where n is an integer greater than 1.

22. The computer program product of claim 21, wherein the pseudo random sequence comprises one of 63 and 127 elements.

23. The computer program product of claim 21, wherein the pseudo random sequence is cycled through once for each k-space line.

24. The computer program product of claim 21, wherein the pseudo random sequence is used to modulate a 180° variable selective pulse applied to the sample.

25. The computer program product of claim 21, wherein the sample is an artery, and wherein arterial longitudinal magnetization and flow distribution are related according to:

$$M_i = \sum_{j=0}^{N-1} (M^0(-1))^{\sum_{k=i}^{i-j} S_k} f_j,$$

wherein $M_i$ is the image observed at the $i^{th}$ element in the pseudo random sequence, $f_j$ is the spins that have taken j TR periods to move from the edge of an inversion slab to an imaging slice location, and $S_k$ is 0 or 1 depending on whether there had been a 180° pulse at a $k^{th}$ step of the pseudo random sequence.

26. The computer program product of claim 21, wherein the number of image slices of the sample acquired equals the length of the pseudo-random sequence.

27. The computer program product of claim 20, wherein the complex sequence is used to modulate a 180° variable selective pulse applied to the sample.

* * * * *